United States Patent
Rheinheimer et al.

(10) Patent No.: US 6,956,034 B2
(45) Date of Patent: Oct. 18, 2005

(54) OXAZIN(ETHYL)ONE COMPOUNDS USED AS FUNGICIDES

(75) Inventors: Joachim Rheinheimer, Ludwigshafen (DE); Andreas Gypser, Mannheim (DE); Ingo Rose, Mannheim (DE); Thomas Grote, Wachenheim (DE); Peter Schäfer, Ottersheim (DE); Frank Schieweck, Hessheim (DE); Eberhard Ammermann, Heppenheim (DE); John-Bryan Speakman, Bobenheim (DE); Siegfried Strathmann, Limburgerhof (DE); Gisela Lorenz, Hambach (DE)

(73) Assignee: BASF Aktiengesellschaft, Ludwigshagen (DE)

( * ) Notice: Subject to any disclaimer, the term of this patent is extended or adjusted under 35 U.S.C. 154(b) by 23 days.

(21) Appl. No.: 10/477,355
(22) PCT Filed: May 17, 2002
(86) PCT No.: PCT/EP02/05499
§ 371 (c)(1), (2), (4) Date: Nov. 12, 2003
(87) PCT Pub. No.: WO02/094797
PCT Pub. Date: Nov. 28, 2002

(65) Prior Publication Data
US 2004/0181061 A1 Sep. 16, 2004

(30) Foreign Application Priority Data
May 21, 2001 (DE) .......................................... 101 24 798

(51) Int. Cl.$^7$ .................... C07D 413/04; C07D 498/04; A61K 31/536; A61K 31/5365
(52) U.S. Cl. ..................... 514/230.5; 544/91; 544/92
(58) Field of Search ................... 544/91, 92; 514/230.5

(56) References Cited

U.S. PATENT DOCUMENTS 3,491,092 A    1/1970   Grigat et al.

FOREIGN PATENT DOCUMENTS

| DE | 1 956 043 | 5/1969 |
|---|---|---|
| DE | 2 218 301 | 10/1973 |
| WO | 00/51992 | 9/2000 |

*Primary Examiner*—Mark L. Berch
*Assistant Examiner*—Kahsay Habte
(74) *Attorney, Agent, or Firm*—Novak Druce & Quigg; Jason D. Voight

(57) ABSTRACT

Oxazin(ethi)one compounds of the formula I:

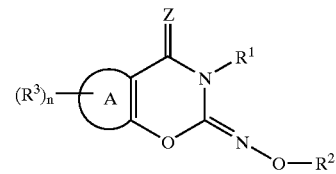

in which the variables Z, $R^1$, $R^2$, $R^3$ and n are as defined in claim 1 and A is a 5- or 6-membered carbocycle or a 5- or 6-membered heterocycle having 1, 2 or 3 heteroatoms selected from the group consisting of N, O and S, each of which cycles is attached via two carbon atoms to the oxazin(ethi)one ring, and the agriculturally useful salts of the oxazin(ethi)one compounds I are described.

Moreover, the invention describes the use of compounds I and their salts for controlling phytopathogenic fungi, compositions which comprise the compounds I and/or their salts in a fungicidally effective amount and a method for controlling phytopathogenic fungi which comprises treating the fungi or the materials, plants, seeds or the soil threatened by fungal attack with a fungicidally effective amount of at least one compound of the formula I as claimed in claim 1 and/or a salt of I.

9 Claims, No Drawings

OXAZIN(ETHYL)ONE COMPOUNDS USED AS FUNGICIDES

The invention relates to novel oxazin(ethi)one compounds and to their use for controlling phytopathogenic fungi, and to compositions for controlling phytopathogenic fungi, which compositions comprise a fungicidally effective amount of these oxazin(ethi)one compounds.

DE-A 2218301 discloses fungicidally active benzo-1-oxa-3-azin-4-ones and benzo-1-thia-3-azin-4-ones which have a trifluoromethylimino group in the 2-position.

WO 00/51992 discloses fungicidally active azinone compounds of the formulae A and B,

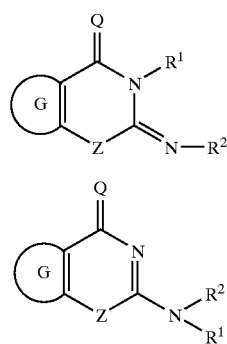

in which Q is oxygen or sulfur and Z is oxygen, sulfur or an N-alkylimine group, G is a fused benzene ring or a fused aromatic heterocycle and $R^1$ and $R^2$ are, inter alia, unsubstituted or substituted alkyl.

Some of the oxazinone-based fungicides known from the prior art are unsatisfactory with respect to their activity and/or selectivity for phytopathogenic fungi.

It is an object of the present invention to provide novel fungicides which allow better control of phytopathogenic fungi than known fungicides. Advantageously, the novel fungicides should be highly active against phytopathogenic fungi.

We have found that this object is achieved by the oxazin (ethi)one compounds of the formula I defined below.

Accordingly, the invention relates to oxazin(ethi)one compounds of the formula I:

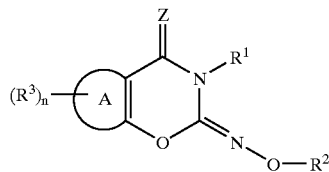

in which the variables Z, $R^1$, $R^2$, $R^3$ and n are as defined below:

Z is oxygen or sulfur, $R^1$ is hydrogen, is $C_1$–$C_6$-alkyl, $C_2$–$C_6$-alkenyl, $C_2$–$C_6$-alkynyl, which are in each case unsubstituted or substituted by O—$R^4$, C(O)O—$R^5$, $NR^6R^7$, C(O)$NR^6R^7$, S—$R^8$, $C_3$–$C_8$-cycloalkyl, phenyl or by 5- or 6-membered saturated or unsaturated heterocyclyl having 1 to 3 heteroatoms selected from the group consisting of N, O and S, where phenyl and heterocyclyl may be mono-, di- or trisubstituted by $C_1$–$C_6$-haloalkyl, $C_2$–$C_6$-haloalkenyl or $C_2$–$C_6$-haloalkynyl;

$R^2$ is $C_1$–$C_3$-alkyl, $C_1$–$C_3$-haloalkyl or cyclopropylmethyl;

$R^3$ is halogen, cyano, $C_1$–$C_6$-alkyl, $C_1$–$C_6$-haloalkyl, $C_1$–$C_6$-alkoxy or $C_1$–$C_6$-haloalkoxy;

n is a number from 0 to 4;

A is a 5- or 6-membered carbocycle or a 5- or 6-membered heterocycle having 1, 2 or 3 heteroatoms selected from the group consisting of N, O and S, each of which cycles is fused to the oxazin(ethi)one ring via two carbon atoms;

$R^4$, $R^5$ independently of one another are hydrogen, $C_1$–$C_6$-alkyl, $C_2$–$C_6$-alkenyl, $C_2$–$C_6$-alkynyl, $C_1$–$C_6$-haloalkyl, $C_2$–$C_6$-haloalkenyl, $C_2$–$C_6$-haloalkynyl, hydroxy-$C_1$–$C_4$-alkyl, hydroxycarbonyl-$C_1$–$C_4$-alkyl, $C_1$–$C_4$-alkoxy-$C_1$–$C_4$-alkyl or $C_1$–$C_4$-alkoxycarbonyl-$C_1$–$C_4$-alkyl;

$R^6$, $R^7$ independently of one another are hydrogen, $C_1$–$C_6$-alkyl, $C_1$–$C_6$-alkoxy, $C_2$–$C_6$-alkenyl, $C_2$–$C_6$-alkynyl, $C_1$–$C_6$-haloalkyl, $C_1$–$C_6$-haloalkoxy, $C_2$–$C_6$-haloalkenyl, $C_2$–$C_6$-haloalkynyl, hydroxy-$C_1$–$C_4$-alkyl, hydroxycarbonyl-$C_1$–$C_4$-alkyl, $C_1$–$C_4$-alkoxy-$C_1$–$C_4$-alkyl or $C_1$–$C_4$-alkoxycarbonyl-$C_1$–$C_4$-alkyl;

$R^6$ and $R^7$ together with the nitrogen atom to which they are attached may also form a 5-, 6- or 7-membered saturated N-heterocycle which may contain a further heteroatom selected from the group consisting of O, N and S and/or which may be substituted by 1 to 4 $C_1$–$C_6$-alkyl groups;

$R^8$ represents $C_1$–$C_6$-alkyl, $C_2$–$C_6$-alkenyl, $C_2$–$C_6$-alkynyl, $C_1$–$C_6$-haloalkyl, $C_2$–$C_6$-haloalkenyl, $C_2$–$C_6$-haloalkynyl, hydroxy-$C_1$–$C_4$-alkyl, hydroxycarbonyl-$C_1$–$C_4$-alkyl, $C_1$–$C_4$-alkoxy-$C_1$–$C_4$-alkyl or $C_1$–$C_4$-alkoxycarbonyl-$C_1$–$C_4$-alkyl;

and the agriculturally useful salts of the oxazin(ethi)one compounds I.

Moreover, the invention relates to
the use of compounds I and their salts for controlling phytopathogenic fungi,
compositions which comprise the compounds I and/or their salts in a fungicidally effective amount, preferably together with at least one carrier,
a method for controlling phytopathogenic fungi, which method comprises treating the fungi or the materials, plants, seeds or the soil threatened by fungal attack with a fungicidally effective amount of at least one compound of the formula I as claimed in claim 1 and/or a salt of I.

With respect to the double bond of the imino group, the compounds of the formula I can have either the E configuration, i.e. the oxygen of the oxazinone ring and the oxygen at the imino nitrogen are trans with respect to the C=N double bond, or a Z configuration (cis arrangement of the oxygen of the oxazinone ring and the oxygen at the imino nitrogen). The invention provides both the E and the Z isomers of I and mixtures thereof. The substituents $R^1$ to $R^3$ can have one or more centers of chirality. In this case, they are present as mixtures of enantiomers or diastereomers. The invention provides both the pure enantiomers or diastereomers and mixtures thereof.

The organic moieties mentioned in the definition of the substituents $R^1$, $R^2$, $R^3$, $R^4$, $R^5$, $R^6$, $R^7$ and $R^8$ or as radicals on cycloalkyl, phenyl or heterocyclic rings are—like the term halogen—collective terms for individual enumerations of the individual group members. All the carbon chains, i.e. all alkyl, haloalkyl, alkoxy, haloalkoxy, alkoxycarbonyl, (halo)alkenyl and (halo)alkynyl groups, and the corresponding moieties in larger groups such as phenylalkyl, cycloalkylalkyl, alkoxyalkyl, alkoxycarbonylalkyl, etc., can be straight-chain or branched, where the prefix $C_n$–$C_m$ indicates in each case the possible number of carbon atoms in the group. Halogenated substituents preferably carry one, two, three, four or five identical or different halogen atoms. Examples of specific meanings are:

halogen: fluorine, chlorine, bromine, iodine;

$C_1$–$C_3$-alkyl: methyl, ethyl, n-propyl, 1-methylethyl (=isopropyl);

$C_1$–$C_6$-alkyl: $C_1$–$C_3$-alkyl as mentioned above, and also, for example, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$–$C_3$-haloalkyl: an alkyl radical having 1 to 3 carbon atoms as mentioned above which is partially or fully substituted by fluorine, chlorine, bromine and/or iodine and preferably substituted by fluorine and/or chlorine (fluoro-, chloro- and fluorochloroalkyl), i.e., for example, $CH_2F$, $CHF_2$, $CF_3$, $CH_2Cl$, dichloromethyl, trichloromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, or 1-(bromomethyl)-2-bromoethyl;

$C_1$–$C_6$-haloalkyl: an alkyl radical having 1 to 6 and preferably 1 to 4 carbon atoms as mentioned above which is partially or fully substituted by fluorine, chlorine, bromine and/or iodine, i.e., for example, one of the radicals mentioned under $C_1$–$C_3$-haloalkyl and also 4-fluorobutyl, 4-chlorobutyl, 4-bromobutyl, nonafluorobutyl, 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl. Among these, particular preference is given to trifluoromethyl, trichloromethyl, dichlorofluoromethyl, difluoromethyl, difluorochloromethyl and 2,2,2-trifluoroethyl;

$C_1$–$C_4$-alkoxy: $OCH_3$, $OC_2H_5$, n-propoxy, $OCH(CH_3)_2$, n-butoxy, $OCH(CH_3)$—$C_2H_5$, $OCH_2$—$CH(CH_3)_2$, $OC(CH_3)_3$, preferably $OCH_3$, $OC_2H_5$, $OCH(CH_3)_2$;

$C_1$–$C_6$-alkoxy: $C_1$–$C_4$-alkoxy as defined above and also n-pentyl, 1-methylbutyloxy, 2-methylbutyloxy, 3-methylbutyloxy, 2,2-dimethylpropyloxy, 1-ethylpropyloxy, n-hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy or 1-ethyl-2-methylpropyloxy, preferably methoxy, ethoxy, n-propyloxy, 1-methylethyl, n-butoxy, 1,1-dimethylethyloxy, n-pentyloxy or n-hexyloxy;

$C_1$–$C_4$-haloalkoxy: a $C_1$–$C_4$-alkoxy radical as mentioned above which is partially or fully substituted by fluorine, chlorine, bromine and/or iodine, preferably by fluorine, i.e., for example, $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy ($OCF_2$—$C_2F_5$), 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy, preferably $OCHF_2$, $OCF_3$, dichlorofluoromethoxy, chlorodifluoromethoxy, 2,2,2-trifluoroethoxy;

$C_1$–$C_6$-haloalkoxy: a $C_1$–$C_6$-alkoxy radical as mentioned above which is partially or fully substituted by fluorine, chlorine, bromine and/or iodine, preferably by fluorine, i.e., for example, one of the $C_1$–$C_4$-haloalkoxy radicals mentioned above and also 5-fluoro-1-pentyloxy, 5-chloro-1-pentyloxy, 5-bromo-1-pentyl, 5-iodo-1-pentyl, 5,5,5-trichloro-1-pentyloxy, undecafluoropentyloxy, 6-fluoro-1-hexyloxy, 6-chloro-1-hexyloxy, 6-bromo-1-hexyloxy, 6-iodo-1-hexyloxy, 6,6,6-trichloro-1-hexyloxy or dodecafluorohexyloxy;

phenyl-$C_1$–$C_4$-alkyl: $C_1$–$C_4$-alkyl which carries a phenyl ring, for example benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl)eth-1-yl, 1-(phenylmethyl)-1-(methyl)eth-1-yl or 1-(phenylmethyl)prop-1-yl, preferably benzyl or 2-phenylethyl;

$C_1$–$C_4$-alkoxy-$C_1$–$C_4$-alkyl: $C_1$–$C_4$-alkyl which is substituted by $C_1$–$C_4$-alkoxy -as mentioned above, i.e., for example, $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1- methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably $CH_2$—$OCH_3$, $CH_2$—$OC_2H_5$, 2-methoxyethyl or 2-ethoxyethyl;

hydroxy-$C_1$–$C_4$-alkyl: $C_1$–$C_4$-alkyl, preferably $C_2$–$C_4$-alkyl, which carries an OH group, for example hydroxymethyl, 2-hydroxyeth-1-yl, 2-hydroxyprop-1-yl, 3-hydroxyprop-1-yl, 1-hydroxyprop-2-yl, 2-hydroxybut-1-yl, 3-hydroxybut-1-yl, 4-hydroxybut-1-yl, 1-hydroxybut-2-yl, 1-hydroxybut-3-yl, 2-hydroxybut-3-yl, 1-hydroxy-2-methylprop-3-yl, 2-hydroxy-2-methylprop-3-yl or 2-hydroxymethylprop-2-yl, in particular 2-hydroxyethyl;

hydroxycarbonyl-$C_1$–$C_4$-alkyl: $C_1$–$C_4$-alkyl, preferably $C_2$–$C_4$-alkyl, which carries a COOH group, for example hydroxycarbonylmethyl, 2-hydroxycarbonyleth-1-yl, 2-hydroxycarbonylprop-1-yl, 3-hydroxycarbonylprop-1-yl, 1-hydroxycarbonylprop-2-yl, 2-hydroxycarbonylbut-1-yl, 3-hydroxycarbonylbut-1-yl, 4-hydroxycarbonylbut-1-yl, 1-hydroxycarbonylbut-2-yl, 1-hydroxycarbonylbut-3-yl, 2-hydroxycarbonylbut-3-yl, 1-hydroxycarbonyl-2-methylprop-3-yl, 2-hydroxycarbonyl-2-methylprop-3-yl or 2-hydroxycarbonyl-1-methylprop-2-yl, in particular 2-hydroxycarbonylethyl;

($C_1$–$C_4$-alkoxy)carbonyl-$C_1$–$C_4$-alkyl: $C_1$–$C_4$-alkyl which is substituted by ($C_1$–$C_4$-alkoxy)carbonyl such as CO—$OCH_3$, CO—$OC_2H_5$, CO—$OCH_2$—$C_2H_5$, CO—$OCH(CH_3)_2$, n-butoxycarbonyl, CO—$OCH(CH_3)$—$C_2H_5$, CO—$OCH_2$—$CH(CH_3)_2$ or CO—$OC(CH_3)_3$, preferably by CO—$OCH_3$ or CO—$OC_2H_5$, i.e., for example, $CH_2$—CO—$OCH_3$, $CH_2$—CO—$OC_2H_5$, $CH_2$—CO—$OCH_2$—$C_2H_5$, $CH_2$—CO—$OCH(CH_3)_2$, n-butoxycarbonylmethyl, $CH_2$—CO—$OCH(CH_3)$—$C_2H_5$, $CH_2$—CO—$OCH_2$—$CH(CH_3)_2$, $CH_2$—CO—$OC(CH_3)_3$, 1-(CO—$OCH_3$)ethyl, 1-(CO—$OC_2H_5$)ethyl, 1-(CO—$OCH_2$—$C_2H_5$)ethyl, 1-[$CH(CH_3)_2$]ethyl, 1-(n-butoxycarbonyl)ethyl, 1-[1-methylpropoxycarbonyl]ethyl, 1-[2-methylpropoxycarbonyl]ethyl, 2-(CO—$OCH_3$)ethyl, 2-(CO—$OC_2H_5$)ethyl, 2-(CO—$OCH_2$—$C_2H_5$)ethyl, 2-[CO—$OCH(CH_3)_2$]ethyl, 2-(n-butoxycarbonyl)ethyl, 2-[1-methylpropoxycarbonyl]ethyl, 2-[2-methylpropoxycarbonyl]ethyl, 2-[CO—$OC(CH_3)_3$]ethyl, 2-(CO—$OCH_3$)propyl, 2-(CO—$OC_2H_5$)propyl, 2-(CO—$OCH_2$—$C_2H_5$)propyl, 2-[CO—$OCH(CH_3)_2$]propyl, 2-(n-butoxycarbonyl)propyl, 2-[1-methylpropoxycarbonyl]propyl, 2-[2-methylpropoxycarbonyl]propyl, 2-[CO—$OC(CH_3)_3$]propyl, 3-(CO—$OCH_3$)propyl, 3-(CO—$OC_2H_5$)propyl, 3-(CO—$OCH_2$—$C_2H_5$)propyl, 3-[CO—$OCH(CH_3)_2$]propyl, 3-(n-butoxycarbonyl)propyl, 3-[1-methylpropoxycarbonyl]propyl, 3-[2-methylpropoxycarbonyl]propyl, 3-[CO—$OC(CH_3)_3$]propyl, 2-(CO—$OCH_3$)butyl, 2-(CO—$OC_2H_5$)butyl, 2-(CO—$OCH_2$—$C_2H_5$)butyl, 2-[CO—$OCH(CH_3)_2$]butyl, 2-(n-butoxycarbonyl)butyl, 2-[1-methylpropoxycarbonyl]butyl, 2-[2-methylpropoxycarbonyl]butyl, 2-[CO—$OC(CH_3)_3$]butyl, 3-(CO—$OCH_3$)butyl, 3-(CO—$OC_2H_5$)butyl, 3-(CO—$OCH_2$—$C_2H_5$)butyl, 3-[CO—$OCH(CH_3)_2$]butyl, 3-(n-butoxycarbonyl)butyl, 3-[1-methylpropoxycarbonyl]butyl, 3-[2-methylpropoxycarbonyl]butyl, 3-[CO—$OC(CH_3)_3$]butyl, 4-(CO—$OCH_3$)butyl, 4-(CO—$OC_2H_5$)butyl, 4-(CO—$OCH_2$—$C_2H_5$)butyl, 4-[CO—$OCH(CH_3)_2$]butyl, 4-(n-butoxycarbonyl)butyl, 4-[1-methylpropoxycarbonyl]butyl, 4-[2-methylpropoxycarbonyl]butyl or 4-[CO—$OC(CH_3)_3$]butyl, preferably $CH_2$—CO—$OCH_3$, $CH_2$—CO—$OC_2H_5$, 1-(CO—$OCH_3$)ethyl or 1-(CO—$OC_2H_5$)ethyl;

$C_2$–$C_6$-alkenyl: straight-chain or branched hydrocarbon radicals having 2 to 6 and preferably 3 to 4 carbon atoms and one double bond in any position, for example ethenyl (vinyl), prop-1-en-1-yl, allyl, 1-methylethenyl, 1-buten-1-yl, 1-buten-2-yl, 1-buten-3-yl, 2-buten-1-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-3-en-1-yl, 2,3-dimethylbut-2-en-1-yl, 2,3-dimethylbut-1-en-1-yl, 3,3-dimethylbut-2-en-1-yl, 1-ethylbut-3-en-1-yl, 1-ethylbut-2-en-1-yl, 1-ethylbut-3-en-1-yl, 2-ethylbut-3-en-1-yl, 2-ethylbut-2-en-1-yl, 2-ethylbut-3-en-1-yl, 1,1,2-trimethylprop-2-en-1-yl, 1-ethyl-2-methylprop-2-en-1-yl, 1-ethyl-2-methylprop-2-en-1-yl or 1-ethyl-2-methylprop-2-en-1-yl;

$C_2$–$C_6$-alkynyl: straight-chain or branched hydrocarbon groups having 2 to 6 and preferably 3 to 4 carbon atoms and one triple bond in any position, for example ethynyl and $C_3$–$C_6$-alkynyl such as prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, preferably prop-2-yn-1-yl;

$C_2$–$C_6$-haloalkenyl: $C_2$–$C_6$-alkenyl, preferably $C_3$–$C_4$-alkenyl, as mentioned above which is partially or fully substituted, preferably mono-, di- or trisubstituted, by halogen, in particular by fluorine, chlorine and/or bromine, i.e., for example, 2-chlorovinyl, 2-chloroallyl, E- and Z-3-chloroallyl, E- and Z-2,3-dichloroallyl, 3,3-dichloroallyl, 2,3,3-trichloroallyl, E- and Z-2,3-dichlorobut-2-enyl, 2-bromoallyl, E- and Z-3-bromoallyl, E- and Z-2,3-dibromoallyl, 3,3-dibromoallyl, 2,3,3-tribromoallyl and E- and Z-2,3-dibromobut-2-enyl;

$C_2$–$C_6$-haloalkynyl: $C_2$–$C_6$-alkynyl, preferably $C_3$–$C_4$-alkynyl, as mentioned above which is partially or fully substituted, preferably mono-, di- or trisubstituted, by halogen, in particular by fluorine, chlorine and/or bromine, i.e., for example, 1,1-difluoroprop-2-yn-1-yl, 1,1-difluorobut-2-yn-1-yl, 4-fluorobut-2-yn-1-yl, 4-chlorobut-2-yn-1-yl, 5-fluoropent-3-yn-1-yl or 6-fluorohex-4-yn-1-yl;

$C_3$–$C_8$-cycloalkyl: cyclopropyl, cyclobutyl, cyclopentyl, cyclohexyl, cycloheptyl or cyclooctyl;

$C_3$–$C_8$-cycloalkyl-$C_1$–$C_4$-alkyl: $C_1$–$C_4$-alkyl which carries a $C_3$–$C_8$-cycloalkyl radical, for example cyclopropylmethyl, 1-cyclopropylethyl, 2-cyclopropylethyl, 1-cyclopropylprop-1-yl, 2-cyclopropylprop-1-yl, 3-cyclopropylprop-1-yl, 1-cyclopropylbut-1-yl, 2-cyclopropylbut-1-yl, 3-cyclopropylbut-1-yl, 4-cyclopropylbut-1-yl, 1-cyclopropylbut-2-yl, 2-cyclopropylbut-2-yl, 3-cyclopropylbut-2-yl, 3-cyclopropylbut-2-yl, 4-cyclopropylbut-2-yl, 1-(cyclopropylmethyl)eth-1-yl, 1-(cyclopropylmethyl)-1-(methyl)eth-1-yl, 1-(cyclopropylmethyl)prop-1-yl, cyclobutylmethyl, 1-cyclobutylethyl, 2-cyclobutylethyl, 1-cyclobutylprop-1-yl, 2-cyclobutylprop-1-yl, 3-cyclobutylprop-1-yl, 1-cyclobutylbut-1-yl, 2-cyclobutylbut-1-yl, 3-cyclobutylbut-1-yl, 4-cyclobutylbut-1-yl, 1-cyclobutylbut-2-yl, 2-cyclobutylbut-2-yl, 3-cyclobutylbut-2-yl, 3-cyclobutylbut-2-yl, 4-cyclobutylbut-2-yl, 1-(cyclobutylmethyl)eth-1-yl, 1-(cyclobutylmethyl)-1-(methyl)eth-1-yl, 1-(cyclobutylmethyl)prop-1-yl, cyclopentylmethyl, 1-cyclopentylethyl, 2-cyclopentylethyl, 1-cyclopentylprop-1-yl, 2-cyclopentylprop-1-yl, 3-cyclopentylprop-1-yl, 1-cyclopentylbut-1-yl, 2-cyclopentylbut-1-yl, 3-cyclopentylbut-1-yl, 4-cyclopentylbut-1-yl, 1-cyclopentylbut-2-yl, 2-cyclopentylbut-2-yl, 3-cyclopentylbut-2-yl, 3-cyclopentylbut-2-yl, 4-cyclopentylbut-2-yl, 1-(cyclopentylmethyl)eth-1-yl, 1-(cyclopentylmethyl)-1-(methyl)eth-1-yl, 1-(cyclopentylmethyl)prop-1-yl, cyclohexylmethyl, 1-cyclohexylethyl, 2-cyclohexylethyl, 1-cyclohexylprop-1-yl, 2-cyclohexylprop-1-yl, 3-cyclohexylprop-1-yl, 1-cyclohexylbut-1-yl, 2-cyclohexylbut-1-yl, 3-cyclohexylbut-1-yl, 4-cyclohexylbut-1-yl, 1-cyclohexylbut-2-yl, 2-cyclohexylbut-2-yl, 3-cyclohexylbut-2-yl, 3-cyclohexylbut-2-yl, 4-cyclohexylbut-2-yl, l-(cyclohexylmethyl)eth-1-yl, 1-(cyclohexylmethyl)-1-(methyl)eth-1-yl, 1-(cyclohexylmethyl)prop-1-yl, cycloheptylmethyl, 1-cycloheptylethyl, 2-cycloheptylethyl, 1-cycloheptylprop-1-yl, 2-cycloheptylprop-1-yl, 3-cycloheptylprop-1-yl, 1-cycloheptylbut-1-yl, 2-cycloheptylbut-1-yl, 3-cycloheptylbut-1-yl, 4-cycloheptylbut-1-yl, 1-cycloheptylbut-2-yl, 2-cycloheptylbut-2-yl, 3-cycloheptylbut-2-yl, 3-cycloheptylbut-2-yl, 4-cycloheptylbut-2-yl, 1-(cycloheptylmethyl)eth-1-yl, 1-(cycloheptylmethyl) -1-(methyl)eth-1-yl, 1-(cycloheptylmethyl)prop-1-yl, cyclooctylmethyl, 1-cyclooctylethyl, 2-cyclooctylethyl, 1-cyclooctylprop-1-yl, 2-cyclooctylprop-1-yl, 3-cyclooctylprop-1-yl, 1-cyclooctylbut-1-yl, 2-cyclooctylbut-1-yl, 3-cyclooctylbut-1-yl, 4-cyclooctylbut-1-yl, 1-cyclooctylbut-2-yl, 2-cyclooctylbut-2-yl, 3-cyclooctylbut-2-yl, 3-cyclooctylbut-2-yl, 4-cyclooctylbut-2-yl, 1-(cyclooctylmethyl)eth-1-yl, 1-(cyclooctylmethyl)-1-(methyl)eth-1-yl or 1-(cyclooctylmethyl)prop-1-yl, preferably cyclopropylmethyl, cyclobutylmethyl, cyclopentylmethyl or cyclohexylmethyl.

Examples of 5- or 6-membered heterocyclyl having 1, 2 or 3 heteroatoms selected from the group consisting of N, O and S include:

unsaturated, in particular aromatic, heterocyclyl, for example furyl such as 2-furyl and 3-furyl, thienyl such as 2-thienyl and 3-thienyl, pyrrolyl such as 2-pyrrolyl and 3-pyrrolyl, isoxazolyl such as 3-isoxazolyl, 4-isoxazolyl and 5-isoxazolyl, isothiazolyl such as 3-isothiazolyl, 4-isothiazolyl and 5-isothiazolyl, pyrazolyl such as 3-pyrazolyl, 4-pyrazolyl and 5-pyrazolyl, oxazolyl such as 2-oxazolyl, 4-oxazolyl and 5-oxazolyl, thiazolyl such as 2-thiazolyl, 4-thiazolyl and 5-thiazolyl, imidazolyl such as 2-imidazolyl and 4-imidazolyl, oxadiazolyl such as 1,2,4-oxadiazol-3-yl, 1,2,4-oxadiazol-5-yl and 1,3,4-oxadiazol-2-yl, thiadiazolyl such as 1,2,4-thiadiazol-3-yl, 1,2,4-thiadiazol-5-yl and 1,3,4-thiadiazol-2-yl, triazolyl such as 1,2,4-triazol-1-yl, 1,2,4-triazol-3-yl and 1,2,4-triazol-4-yl, pyridinyl such as 2-pyridinyl, 3-pyridinyl and 4-pyridinyl, pyridazinyl such as 3-pyridazinyl and 4-pyridazinyl, pyrimidinyl such as 2-pyrimidinyl, 4-pyrimidinyl and 5-pyrimidinyl, furthermore 2-pyrazinyl, 1,3,5-triazin-2-yl and 1,2,4-triazin-3-yl, in particular pyridyl, pyrimidyl, furyl and thienyl;

saturated heterocyclyl, for example tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl.

Substituents on phenyl or heterocyclyl are usually selected from the group consisting of halogen, $C_1$–$C_4$-alkyl, $C_1$–$C_4$-haloalkyl, $C_1$–$C_4$-alkoxy, $C_1$–$C_4$-haloalkoxy, methylenedioxy, CN and $C_1$–$C_4$-alkylcarbonyl.

In the formula I, the variable A or the structural element

denotes a 5- or 6-membered carbocycle or a 5- or 6-membered heterocycle having 1, 2 or 3 heteroatoms selected from the group consisting of N, O and S, which cycles are fused to the oxazin(ethi)one ring via two carbon atoms. In this representation of the formula of the variable A, the two * positions denote the carbon atoms which are shared by the oxazin(ethi)one ring and the ring fused with the oxazin(ethi)one ring. Examples of fused 5- or 6-membered carbocycles are, in addition to benzene, also cyclohexene, 1,3- and 1,4-cyclohexanediene and cyclopentene. Examples of fused 5- or 6-membered heterocycles are the heteroaromatic groups mentioned above which have two adjacent carbon ring members and their di- and tetrahydro derivatives which retain at least one C=C double bond, for example pyridine, pyrazine, pyridazine, pyrimidine, furan, dihydrofuran, thiophene, thiophene dioxide, 2,3- and 2,5-dihydrothiophene, 2,3- and 2,5-dihydrothiophene dioxide, pyrrole, dihydropyrrole, 1,3-dioxolane, isoxazole, oxazole, 2,3-dihydrooxazole, isothiazole, thiazole, pyrazole, pyrazoline, imidazole, 2,3-dihydroimidazole, 1,2,3-triazole, 1,1-dioxo-2,3-dihydroisothiazole, 2,3-dihydro-1,4-dioxine, 2,3-dihydro-1,4-oxazine, 2,4- and 2,6-dihydro-1,3-oxazine, 2,3-dihydro-1,4-thiazine and 2,4-dihydro-1,3-thiazine.

Preferred fused rings A are aromatic and are in particular selected from the rings of the formulae A1 to A37 shown below:

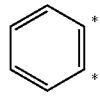 (A1)

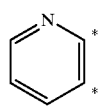 (A2)

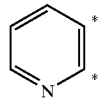 (A3)

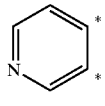 (A4)

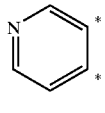 (A5)

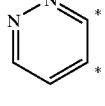 (A6)

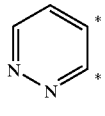 (A7)

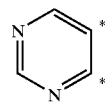 (A8)

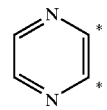 (A9)

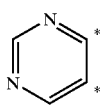 (A10)

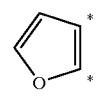 (A11)

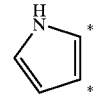 (A12)

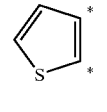 (A13)

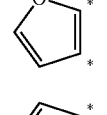 (A14)

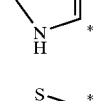 (A15)

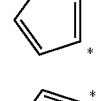 (A16)

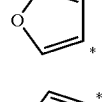 (A17)

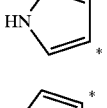 (A18)

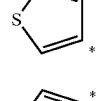 (A19)

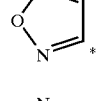 (A20)

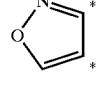 (A21)

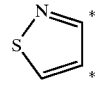 (A22)

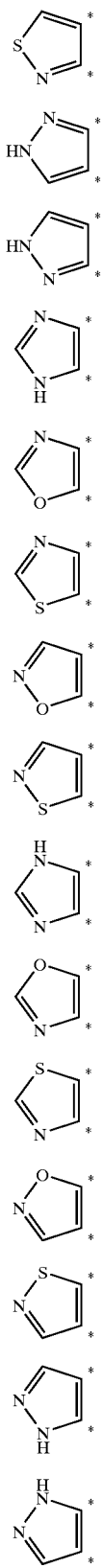

(A23)
(A24)
(A25)
(A26)
(A27)
(A28)
(A29)
(A30)
(A31)
(A32)
(A33)
(A34)
(A35)
(A36)
(A37)

Here, the rings A24 and A37, A25 and A36 and A26 and A31 are in each case tautomers of one another.

In the compounds of the formula I according to the invention, the radicals A, for example the radicals A1 to A37, can be unsubstituted or, depending on the number of free valencies, carry 1, 2, 3 or 4, preferably 1 or 2, identical or different substituents $R^3$. Here, the number of substituents $R^3$ is indicated by the variable n. In the radicals of the formulae A12, A15, A18, A24, A25, A26, A31, A36 and A37, the hydrogen atom located at the nitrogen can also be replaced by a substituent $R^3$, where $R^3$ in this case is alkyl or haloalkyl.

6-membered rings A such as benzene or pyridine preferably carry a substituent $R^3$ in the 6-position (the position meta to the carbon atom which carries the group C=Z), unless there is a heteroatom in this position.

With respect to the fungicidal activity of the compounds I, the substituents Z, $R^1$, $R^2$, $R^3$ and the index n independently of one another, but preferably in combination with one another, have the following meanings:

Z is oxygen;

$R^1$ is $C_1$–$C_6$-alkyl, $C_2$–$C_6$-alkenyl, $C_1$–$C_6$-haloalkyl, $C_2$–$C_6$-haloalkenyl, $C_1$–$C_6$-alkyl which is substituted by $OR^4$ or by $C_3$–$C_8$-cycloalkyl-$C_1$–$C_4$-alkyl. Here, $R^4$ has the meanings given above and is in particular $C_1$–$C_4$-alkyl. $R^1$ is in particular $C_3$–$C_6$-alkyl, $C_3$–$C_4$-alkenyl, $C_3$–$C_4$-alkynyl or $C_3$–$C_6$-cycloalkylmethyl;

$R^2$ is $C_1$–$C_3$-alkyl, $C_1$–$C_3$-fluoroalkyl, $C_1$–$C_3$-fluoro/chloroalkyl or cyclopropylmethyl;

$R^3$ is $C_1$–$C_4$-alkyl, in particular methyl, $C_1$–$C_4$-haloalkyl, in particular difluoromethyl, trifluoromethyl or 2,2,2-trifluoroethyl, $C_1$–$C_4$-haloalkoxy, in particular difluoromethoxy, or, particularly preferably, halogen. Very particular preference is given to chlorine, bromine or iodine;

n is 1, 2, 3 or 4, in particular 1 or 2.

The fused cycle A is selected in particular from the group consisting of benzene (formula A1), pyridine (formulae A2 to A5) and thiophene (formulae A13, A16 and A19).

If $R^1$ denotes $COOR^5$-substituted alkyl, alkenyl or alkynyl, $R^5$ is preferably $C_1$–$C_4$-alkyl. If $R^1$ denotes C(O)$NR^6R^7$-substituted $C_1$–$C_6$-alkyl, -alkenyl or -alkynyl, $R^6$ is preferably hydrogen or $C_1$–$C_4$-alkyl and $R^7$ is preferably hydrogen. If $R^1$ denotes $NR^6R^7$-substituted $C_1$–$C_6$-alkyl, -alkenyl or -alkynyl, $R^6$ and $R^7$ independently of one another are preferably hydrogen or $C_1$–$C_4$-alkyl or $R^6$ and $R^7$ together with the nitrogen atom to which they are attached form a morpholine, piperidine, piperazine or pyrrolidine ring. If $R^1$ denotes $SR^8$-substituted $C_1$–$C_6$-alkyl, -alkenyl or -alkynyl, $R^8$ is preferably $C_1$–$C_4$-alkyl.

Particularly preferred compounds I are the compounds of the formula I-A1

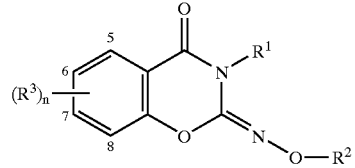

(I-A1)

in which n, $R^1$, $R^2$ and $R^3$ are as defined below:

$R^1$ is $C_1$–$C_6$-alkyl, $C_2$–$C_6$-alkenyl, $C_1$–$C_6$-haloalkyl, $C_2$–$C_6$-haloalkenyl, $C_1$–$C_4$-alkoxy-$C_1$–$C_4$-alkyl or $C_3$–$C_6$-cycloalkyl-$C_1$–$C_4$-alkyl, especially $C_3$–$C_6$-alkyl, $C_3$–$C_4$-alkenyl, $C_3$–$C_4$-haloalkenyl, $C_1$–$C_4$-alkoxyalkyl and $C_3$–$C_6$-cycloalkylmethyl;

$R^2$ is $C_1$–$C_3$-alkyl or $C_1$–$C_3$-haloalkyl;

$R^3$ is $C_1$–$C_4$-alkyl, $C_1$–$C_4$-haloalkyl, in particular difluoromethyl, trifluoromethyl or 2,2,2-trifluoroethyl, $C_1$–$C_4$-haloalkoxy, in particular difluoromethoxy, or, particularly preferably, halogen. Very particular preference is given to chlorine, bromine or iodine;

n is 1 or 2.

Among these, particular preference is given to compounds I-A1 in which one of the substituents $R^3$ is located in the 6-position.

Particular preference is also given to compounds of the formula I-A1 in which $R^2$ is cyclopropylmethyl and $R^1$, $R^3$ and n are as defined above.

Examples of particularly preferred compounds of the formula I-A1 are the compounds I-A1.1 to I-A1.128 in which the variables $R^1$, $R^2$ and $R^3$ in each case have the meanings given in one row of Table 1.

TABLE 1

|  | $R^1$ | $R^2$ | n | $R^3$ |
|---|---|---|---|---|
| I-A1.1 | n-propyl | methyl | 1 | 6-fluoro |
| I-A1.2 | n-propyl | methyl | 1 | 6-chloro |
| I-A1.3 | n-propyl | methyl | 1 | 6-bromo |
| I-A1.4 | n-propyl | methyl | 1 | 6-iodo |
| I-A1.5 | n-propyl | ethyl | 1 | 6-fluoro |
| I-A1.6 | n-propyl | ethyl | 1 | 6-chloro |
| I-A1.7 | n-propyl | ethyl | 1 | 6-bromo |
| I-A1.8 | n-propyl | ethyl | 1 | 6-iodo |
| I-A1.9 | n-propyl | n-propyl | 1 | 6-fluoro |
| I-A1.10 | n-propyl | n-propyl | 1 | 6-chloro |
| I-A1.11 | n-propyl | n-propyl | 1 | 6-bromo |
| I-A1.12 | n-propyl | n-propyl | 1 | 6-iodo |
| I-A1.13 | n-propyl | 2,2,2-trifluoromethyl | 1 | 6-fluoro |
| I-A1.14 | n-propyl | 2,2,2-trifluoromethyl | 1 | 6-chloro |
| I-A1.15 | n-propyl | 2,2,2-trifluoromethyl | 1 | 6-bromo |
| I-A1.16 | n-propyl | 2,2,2-trifluoromethyl | 1 | 6-iodo |
| I-A1.17 | n-butyl | methyl | 1 | 6-fluoro |
| I-A1.18 | n-butyl | methyl | 1 | 6-chloro |
| I-A1.19 | n-butyl | methyl | 1 | 6-bromo |
| I-A1.20 | n-butyl | methyl | 1 | 6-iodo |
| I-A1.21 | n-butyl | ethyl | 1 | 6-fluoro |
| I-A1.22 | n-butyl | ethyl | 1 | 6-chloro |
| I-A1.23 | n-butyl | ethyl | 1 | 6-bromo |
| I-A1.24 | n-butyl | ethyl | 1 | 6-iodo |
| I-A1.25 | n-butyl | n-propyl | 1 | 6-fluoro |
| I-A1.26 | n-butyl | n-propyl | 1 | 6-chloro |
| I-A1.27 | n-butyl | n-propyl | 1 | 6-bromo |
| I-A1.28 | n-butyl | n-propyl | 1 | 6-iodo |
| I-A1.29 | n-butyl | 2,2,2-trifluoromethyl | 1 | 6-fluoro |
| I-A1.30 | n-butyl | 2,2,2-trifluoromethyl | 1 | 6-chloro |
| I-A1.31 | n-butyl | 2,2,2-trifluoromethyl | 1 | 6-bromo |
| I-A1.32 | n-butyl | 2,2,2-trifluoromethyl | 1 | 6-iodo |
| I-A1.33 | 2-butyl | methyl | 1 | 6-fluoro |
| I-A1.34 | 2-butyl | methyl | 1 | 6-chloro |
| I-A1.35 | 2-butyl | methyl | 1 | 6-bromo |
| I-A1.36 | 2-butyl | methyl | 1 | 6-iodo |
| I-A1.37 | 2-butyl | ethyl | 1 | 6-fluoro |
| I-A1.38 | 2-butyl | ethyl | 1 | 6-chloro |
| I-A1.39 | 2-butyl | ethyl | 1 | 6-bromo |
| I-A1.40 | 2-butyl | ethyl | 1 | 6-iodo |
| I-A1.41 | 2-butyl | n-propyl | 1 | 6-fluoro |
| I-A1.42 | 2-butyl | n-propyl | 1 | 6-chloro |
| I-A1.43 | 2-butyl | n-propyl | 1 | 6-bromo |
| I-A1.44 | 2-butyl | n-propyl | 1 | 6-iodo |
| I-A1.45 | 2-butyl | 2,2,2-trifluoromethyl | 1 | 6-fluoro |
| I-A1.46 | 2-butyl | 2,2,2-trifluoromethyl | 1 | 6-chloro |
| I-A1.47 | 2-butyl | 2,2,2-trifluoromethyl | 1 | 6-bromo |
| I-A1.48 | 2-butyl | 2,2,2-trifluoromethyl | 1 | 6-iodo |
| I-A1.49 | isobutyl | methyl | 1 | 6-fluoro |
| I-A1.50 | isobutyl | methyl | 1 | 6-chloro |
| I-A1.51 | isobutyl | methyl | 1 | 6-bromo |
| I-A1.52 | isobutyl | methyl | 1 | 6-iodo |
| I-A1.53 | isobutyl | ethyl | 1 | 6-fluoro |
| I-A1.54 | isobutyl | ethyl | 1 | 6-chloro |
| I-A1.55 | isobutyl | ethyl | 1 | 6-bromo |
| I-A1.56 | isobutyl | ethyl | 1 | 6-iodo |
| I-A1.57 | isobutyl | n-propyl | 1 | 6-fluoro |
| I-A1.58 | isobutyl | n-propyl | 1 | 6-chloro |
| I-A1.59 | isobutyl | n-propyl | 1 | 6-bromo |
| I-A1.60 | isobutyl | n-propyl | 1 | 6-iodo |
| I-A1.61 | isobutyl | 2,2,2-trifluoromethyl | 1 | 6-fluoro |
| I-A1.62 | isobutyl | 2,2,2-trifluoromethyl | 1 | 6-chloro |
| I-A1.63 | isobutyl | 2,2,2-trifluoromethyl | 1 | 6-bromo |
| I-A1.64 | isobutyl | 2,2,2-trifluoromethyl | 1 | 6-iodo |
| I-A1.65 | cyclopropylmethyl | methyl | 1 | 6-fluoro |
| I-A1.66 | cyclopropylmethyl | methyl | 1 | 6-chloro |
| I-A1.67 | cyclopropylmethyl | methyl | 1 | 6-bromo |
| I-A1.68 | cyclopropylmethyl | methyl | 1 | 6-iodo |
| I-A1.69 | cyclopropylmethyl | ethyl | 1 | 6-fluoro |
| I-A1.70 | cyclopropylmethyl | ethyl | 1 | 6-chloro |
| I-A1.71 | cyclopropylmethyl | ethyl | 1 | 6-bromo |
| I-A1.72 | cyclopropylmethyl | ethyl | 1 | 6-iodo |
| I-A1.73 | cyclopropylmethyl | n-propyl | 1 | 6-fluoro |
| I-A1.74 | Cyclopropylmethyl | n-propyl | 1 | 6-chloro |
| I-A1.75 | cyclopropylmethyl | n-propyl | 1 | 6-bromo |
| I-A1.76 | cyclopropylmethyl | n-propyl | 1 | 6-iodo |
| I-A1.77 | cyclopropylmethyl | 2,2,2-trifluoromethyl | 1 | 6-fluoro |
| I-A1.78 | cyclopropylmethyl | 2,2,2-trifluoromethyl | 1 | 6-chloro |
| I-A1.79 | cyclopropylmethyl | 2,2,2-trifluoromethyl | 1 | 6-bromo |
| I-A1.80 | cyclopropylmethyl | 2,2,2-trifluoromethyl | 1 | 6-iodo |
| I-A1.81 | E-3-chloro-2-propenyl | methyl | 1 | 6-fluoro |
| I-A1.82 | E-3-chloro-2-propenyl | methyl | 1 | 6-chloro |
| I-A1.83 | E-3-chloro-2-propenyl | methyl | 1 | 6-bromo |
| I-A1.84 | E-3-chloro-2-propenyl | methyl | 1 | 6-iodo |
| I-A1.85 | E-3-chloro-2-propenyl | ethyl | 1 | 6-fluoro |
| I-A1.86 | E-3-chloro-2-propenyl | ethyl | 1 | 6-chloro |
| I-A1.87 | E-3-chloro-2-propenyl | ethyl | 1 | 6-bromo |
| I-A1.88 | E-3-chloro-2-propenyl | ethyl | 1 | 6-iodo |
| I-A1.89 | E-3-chloro-2-propenyl | n-propyl | 1 | 6-fluoro |
| I-A1.90 | E-3-chloro-2-propenyl | n-propyl | 1 | 6-chloro |
| I-A1.91 | E-3-chloro-2-propenyl | n-propyl | 1 | 6-bromo |
| I-A1.92 | E-3-chloro-2-propenyl | n-propyl | 1 | 6-iodo |
| I-A1.93 | E-3-chloro-2-propenyl | 2,2,2-trifluoromethyl | 1 | 6-fluoro |
| I-A1.94 | E-3-chloro-2-propenyl | 2,2,2-trifluoromethyl | 1 | 6-chloro |
| I-A1.95 | E-3-chloro-2-propenyl | 2,2,2-trifluoromethyl | 1 | 6-bromo |
| I-A1.96 | E-3-chloro-2-propenyl | 2,2,2-trifluoromethyl | 1 | 6-iodo |
| I-A1.97 | $CH_2$—CH=$CH_3$ | methyl | 1 | 6-fluoro |
| I-A1.98 | $CH_2$—CH=$CH_3$ | methyl | 1 | 6-chloro |
| I-A1.99 | $CH_2$—CH=$CH_3$ | methyl | 1 | 6-bromo |
| I-A1.100 | $CH_2$—CH=$CH_3$ | methyl | 1 | 6-iodo |
| I-A1.101 | $CH_2$—CH=$CH_3$ | ethyl | 1 | 6-fluoro |
| I-A1.102 | $CH_2$—CH=$CH_3$ | ethyl | 1 | 6-chloro |
| I-A1.103 | $CH_2$—CH=$CH_3$ | ethyl | 1 | 6-bromo |
| I-A1.104 | $CH_2$—CH=$CH_3$ | ethyl | 1 | 6-iodo |
| I-A1.105 | $CH_2$—CH=$CH_3$ | n-propyl | 1 | 6-fluoro |
| I-A1.106 | $CH_2$—CH=$CH_3$ | n-propyl | 1 | 6-chloro |
| I-A1.107 | $CH_2$—CH=$CH_3$ | n-propyl | 1 | 6-bromo |
| I-A1.108 | $CH_2$—CH=$CH_3$ | n-propyl | 1 | 6-iodo |

TABLE 1-continued

| | R¹ | R² | n | R³ |
|---|---|---|---|---|
| I-A1.109 | CH₂—CH=CH₂ | 2,2,2-trifluoromethyl | 1 | 6-fluoro |
| I-A1.110 | CH₂—CH=CH₂ | 2,2,2-trifluoromethyl | 1 | 6-chloro |
| I-A1.111 | CH₂—CH=CH₂ | 2,2,2-trifluoromethyl | 1 | 6-bromo |
| I-A1.112 | CH₂—CH=CH₂ | 2,2,2-trifluoromethyl | 1 | 6-iodo |
| I-A1.113 | CH₂C≡CH | methyl | 1 | 6-fluoro |
| I-A1.114 | CH₂C≡CH | methyl | 1 | 6-chloro |
| I-A1.115 | CH₂C≡CH | methyl | 1 | 6-bromo |
| I-A1.116 | CH₂C≡CH | methyl | 1 | 6-iodo |
| I-A1.117 | CH₂C≡CH | ethyl | 1 | 6-fluoro |
| I-A1.118 | CH₂C≡CH | ethyl | 1 | 6-chloro |
| I-A1.119 | CH₂C≡CH | ethyl | 1 | 6-bromo |
| I-A1.120 | CH₂C≡CH | ethyl | 1 | 6-iodo |
| I-A1.121 | CH₂C≡CH | n-propyl | 1 | 6-fluoro |
| I-A1.122 | CH₂C≡CH | n-propyl | 1 | 6-chloro |
| I-A1.123 | CH₂C≡CH | n-propyl | 1 | 6-bromo |
| I-A1.124 | CH₂C≡CH | n-propyl | 1 | 6-iodo |
| I-A1.125 | CH₂C≡CH | 2,2,2-trifluoromethyl | 1 | 6-fluoro |
| I-A1.126 | CH₂C≡CH | 2,2,2-trifluoromethyl | 1 | 6-chloro |
| I-A1.127 | CH₂C≡CH | 2,2,2-trifluoromethyl | 1 | 6-bromo |
| I-A1.128 | CH₂C≡CH | 2,2,2-trifluoromethyl | 1 | 6-iodo |
| I-A1.129 | n-propyl | n-propyl | 0 | |
| I-A1.130 | n-propyl | n-propyl | 1 | 6-methyl |
| I-A1.131 | methyl | n-propyl | 1 | 6-methyl |
| I-A1.132 | n-propyl | methyl | 1 | 6-methyl |
| I-A1.133 | n-propyl | methyl | 1 | 6-methoxy |
| I-A1.134 | cyclopropylmethyl | 2-propyl | 1 | 6-iodo |
| I-A1.135 | cyclopropylmethyl | cyclopropylmethyl | 1 | 6-iodo |
| I-A1.136 | n-butyl | cyclopropylmethyl | 1 | 6-iodo |
| I-A1.137 | n-propyl | cyclopropylmethyl | 1 | 6-iodo |
| I-A1.138 | n-butyl | 2-propyl | 1 | 6-iodo |
| I-A1.139 | n-propyl | 2-propyl | 1 | 6-iodo |

In Table 1 and in Tables 2 and 3 below, the prefix of the substituent denotes its position in the fused ring A.

Particular preference is furthermore given to the compounds of the formulae I-A13, I-A16 and I-A19

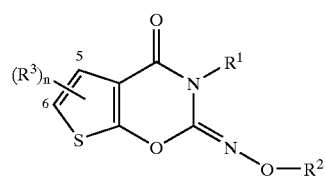
(I-A13)

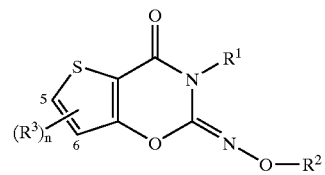
(I-A16)

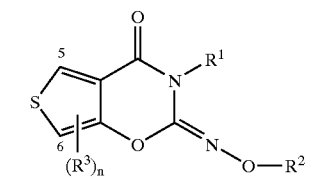
(I-A19)

in which n, $R^1$, $R^2$ and $R^3$ are as defined below:

$R^1$ is $C_1$–$C_6$-alkyl, $C_2$–$C_6$-alkenyl, $C_1$–$C_6$-haloalkyl, $C_2$–$C_6$-haloalkenyl, $C_1$–$C_4$-alkoxy-$C_1$–$C_4$-alkyl or $C_3$–$C_6$-cycloalkyl-$C_1$–$C_4$-alkyl, especially $C_3$–$C_6$-alkyl, $C_3$–$C_4$-alkenyl, $C_3$–$C_4$-haloalkenyl, $C_1$–$C_4$-alkoxyalkyl and $C_3$–$C_6$-cycloalkylmethyl;

$R^2$ is $C_1$–$C_3$-alkyl or $C_1$–$C_3$-haloalkyl;

$R^3$ is $C_1$–$C_4$-alkyl, in particular methyl, $C_1$–$C_4$-haloalkyl, in particular difluoromethyl, trifluoromethyl or 2,2,2-trifluoroethyl, $C_1$–$C_4$-haloalkoxy, in particular difluoromethoxy, or, particularly preferably, halogen. Very particular preference is given to chlorine, bromine or iodine;

n is 1 or 2.

Particular preference is also given to the compounds of the formulae I-A13, I-A16 and I-A19 in which $R^2$ is cyclopropylmethyl and $R^1$, $R^3$ and n are as defined above.

Examples of particularly preferred compounds of the formulae I-A13, I-A16 and I-A19 are the compounds in which the variables $R^1$, $R^2$ and $R^3$ in each case have the meanings given in one row of Table 2 (compounds I-A13.1 to I-A13.18, I-A16.1 to I-A16.18 and I-A19.1 to I-A19.18).

TABLE 2

| | R¹ | R² | n | R³ |
|---|---|---|---|---|
| 1 | n-propyl | methyl | 1 | 5-chloro |
| 2 | n-propyl | methyl | 1 | 6-chloro |
| 3 | n-propyl | methyl | 0 | — |
| 4 | n-butyl | methyl | 1 | 5-chloro |
| 5 | n-butyl | methyl | 1 | 6-chloro |
| 6 | n-butyl | methyl | 0 | — |
| 7 | n-propyl | ethyl | 1 | 5-chloro |
| 8 | n-propyl | ethyl | 1 | 6-chloro |
| 9 | n-propyl | ethyl | 0 | — |
| 10 | n-butyl | ethyl | 1 | 5-chloro |
| 11 | n-butyl | ethyl | 1 | 6-chloro |
| 12 | n-butyl | ethyl | 0 | — |
| 13 | n-propyl | n-propyl | 1 | 5-chloro |
| 14 | n-propyl | n-propyl | 1 | 6-chloro |
| 15 | n-propyl | n-propyl | 0 | — |
| 16 | n-butyl | n-propyl | 1 | 5-chloro |
| 17 | n-butyl | n-propyl | 1 | 6-chloro |
| 18 | n-butyl | n-propyl | 0 | — |

Examples of preferred compounds I are furthermore the compounds of the general formula I-A2 in which the variables $R^1$, $R^2$ and $R^3$ in each case have the meanings given in one row of Table 2 (compounds I-A2.1 to I-A2.18).

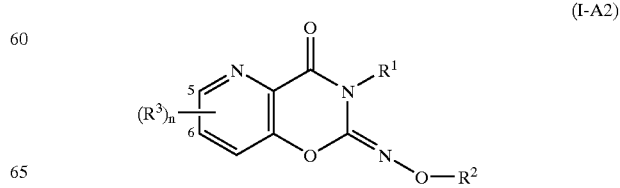
(I-A2)

Examples of preferred compounds I are furthermore the compounds of the general formula I-A3 in which the variables $R^1$, $R^2$ and $R^3$ in each case have the meanings given in one row of Table 2 (compounds I-A3.1 to I-A3.18).

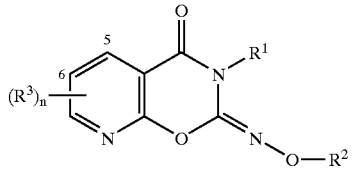
(I-A3)

Examples of preferred compounds I are furthermore the compounds of the general formula I-A4 in which the variables $R^1$, $R^2$ and $R^3$ in each case have the meanings given in one row of Table 2 (compounds I-A4.1 to I-A4.18).

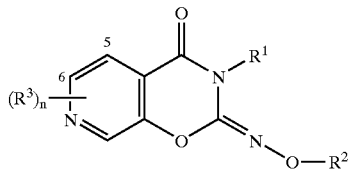
(I-A4)

Examples of preferred compounds I are furthermore the compounds of the general formula I-A5 in which the variables $R^1$, $R^2$ and $R^3$ in each case have the meanings given in one row of Table 2 (compounds I-A5.1 to I-A5.18).

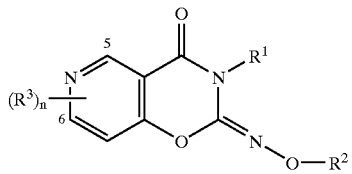
(I-A5)

Further examples of compounds I according to the invention are the compounds of the general formulae I-A6, I-A9, I-A10, I-A11, I-A12, I-A14, I-A15, I-A17, I-A18, I-A20 to I-A27, I-A31, I-A33, I-A36, I-A37 where the variables $R^1$, $R^2$ and R' or R" in each case have the meanings given in one of rows 1 to 27 or 19 to 36 of Table 3.

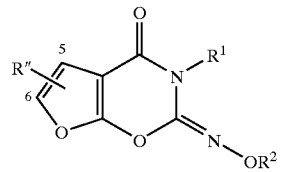
(I-A11)

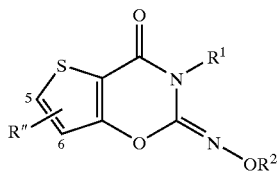
(I-A14)

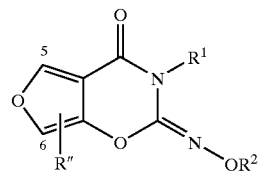
(I-A17)

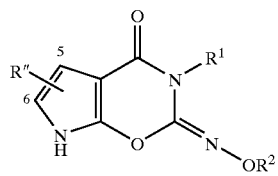
(I-A15)

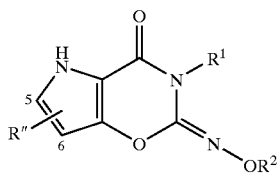
(I-A12)

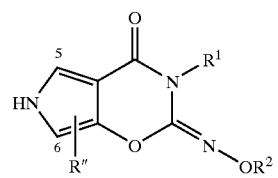
(I-A18)

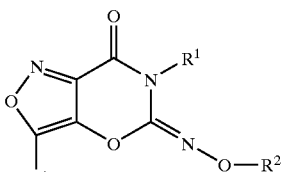
(I-A21)

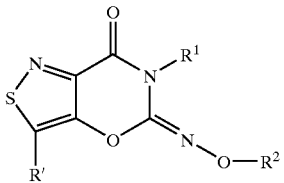
(I-A22)

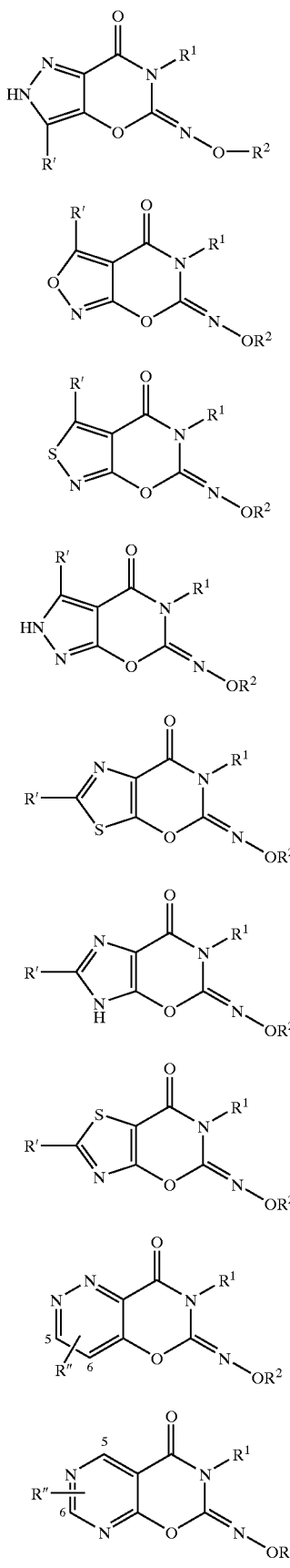

TABLE 3

| | R¹ | R² | n | R' | R" |
|---|---|---|---|---|---|
| 1 | n-propyl | methyl | 1 | — | 5-chloro |
| 2 | n-propyl | methyl | 1 | — | 6-chloro |
| 3 | n-butyl | methyl | 1 | — | 5-chloro |
| 4 | n-butyl | methyl | 1 | — | 6-chloro |
| 5 | n-propyl | ethyl | 1 | — | 5-chloro |
| 6 | n-propyl | ethyl | 1 | — | 6-chloro |
| 7 | n-butyl | ethyl | 1 | — | 5-chloro |
| 8 | n-butyl | ethyl | 1 | — | 6-chloro |
| 9 | n-propyl | n-propyl | 1 | — | 5-chloro |
| 10 | n-propyl | n-propyl | 1 | — | 6-chloro |
| 11 | n-butyl | n-propyl | 1 | — | 5-chloro |
| 12 | n-butyl | n-propyl | 1 | — | 6-chloro |
| 13 | cyclopropylmethyl | methyl | 1 | — | 5-chloro |
| 14 | cyclopropylmethyl | methyl | 1 | — | 6-chloro |
| 15 | cyclopropylmethyl | ethyl | 1 | — | 5-chloro |
| 16 | cyclopropylmethyl | ethyl | 1 | — | 6-chloro |
| 17 | cyclopropylmethyl | n-propyl | 1 | — | 5-chloro |
| 18 | cyclopropylmethyl | n-propyl | 1 | — | 6-chloro |
| 19 | n-propyl | methyl | 0 | | H |
| 20 | n-butyl | methyl | 0 | | H |
| 21 | n-propyl | ethyl | 0 | | H |
| 22 | n-butyl | ethyl | 0 | | H |
| 23 | n-propyl | n-propyl | 0 | | H |
| 24 | n-butyl | n-propyl | 0 | | H |
| 25 | cyclopropylmethyl | methyl | 0 | | H |
| 26 | cyclopropylmethyl | ethyl | 0 | | H |
| 27 | cyclopropylmethyl | n-propyl | 0 | | H |
| 28 | n-propyl | methyl | 1 | chloro | — |
| 29 | n-butyl | methyl | 1 | chloro | — |
| 30 | cyclopropylmethyl | methyl | 1 | chloro | — |
| 31 | n-propyl | ethyl | 1 | chloro | — |
| 32 | n-butyl | ethyl | 1 | chloro | — |
| 33 | cyclopropylmethyl | n-propyl | 1 | chloro | — |
| 34 | n-propyl | n-propyl | 1 | chloro | — |
| 35 | n-butyl | n-propyl | 1 | chloro | — |
| 36 | cyclopropylmethyl | n-propyl | 1 | chloro | — |

The oxazinone compounds of the formula I can be prepared in a manner analogous to a process described in the literature (see Chemische Berichte 97, (1964), p. 3012 and 98, (1965), p. 144) shown in scheme 1. In scheme 1, the variables $R^1$, $R^2$, $R^3$, n and A are as defined above. Y denotes a nucleophilically displaceable leaving group.

Scheme 1:

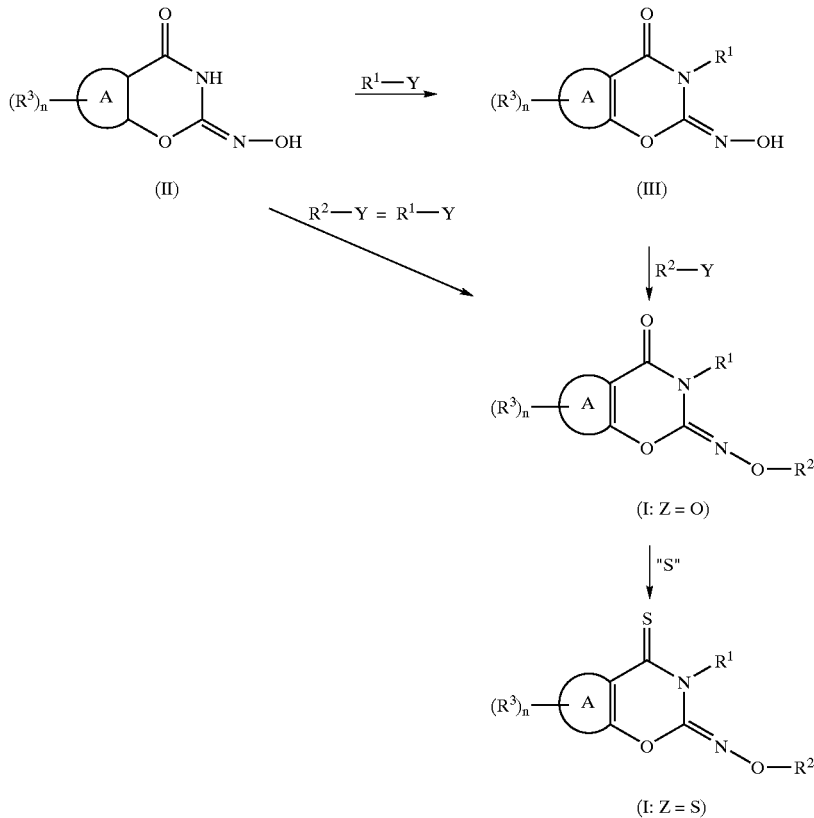

To this end, the 2-hydroxyiminooxazinones of the formula II are alkylated successively to give the compounds I. If $R^1$ and $R^2$ are identical, the alkylation can be carried out in one step.

Otherwise, the alkylation is carried out in two successive steps. Usually, the alkylation at the ring nitrogen atom of II is carried out first by reacting II with an alkylating agent $R^1$—Y, and the oxygen atom of the hydroxyimino group is attached afterward (shown in scheme 1). However, depending on the substrates and reaction conditions, the order may also be changed so that the oxazinone compounds I where $R^1$=H and Z=O are initially obtained which are then alkylated with an alkylating agent $R^1$—Y to give the compound I where $R^1 \neq H$ and Z=O (not shown in scheme 1). By simple preliminary experiments, the person skilled in the art can easily determine which alkylation sequence is more suitable for preparing the compound I.

Suitable alkylating agents are compounds in which the radicals $R^1$ or $R^2$ are attached to a suitable, i.e. nucleophilically displaceable, leaving group. Customary leaving groups are, for example, the following radicals: chlorine, bromine, iodine, methylsulfonyloxy, phenylsulfonyloxy, toluenesulfonyloxy, trifluoromethylsulfonyloxy. In general, the alkylating agent is employed in at least the required stoichiometric amount, i.e. in an equimolar amount, preferably in an amount of from 1 to 2 mol per mole of compound II or III. Volatile alkylating agents can also be employed in a relatively large excess. If $R^1$ and $R^2$ are identical and the alkylation of the ring nitrogen and the hydroxyl function are to be effected simultaneously, at least 2 mol of alkylating agent are employed correspondingly per mole of compound II.

The alkylations are preferably carried out in the presence of a base. Suitable bases are, in principle, all basic compounds capable of deprotonating the amide group or the hydroxyl group of the hydroxyimino function of II or III. These include the alkoxides, amides, hydrides, hydroxides, carbonates and bicarbonates of alkali metals or alkaline earth metals, in particular of lithium, potassium, sodium or calcium. Examples are the sodium or potassium alkoxides of methanol, of ethanol, of n-propanol, of isopropanol, of n-butanol and of tert-butanol, furthermore sodium hydride, calcium hydride, sodium amide, potassium amide, sodium carbonate, potassium carbonate, cesium carbonate, calcium carbonate, sodium bicarbonate, potassium bicarbonate, sodium hydroxide, potassium hydroxide, lithium hydroxide, lithium diisopropylamide. Also suitable are tertiary amines such as triethylamine, pyridine, etc. Furthermore suitable are organolithium compounds such as methyllithium, n-butyllithium, n-hexyllithium, phenyllithium, or Grignard reagents, for example of methane, ethane, butane, hexane, cyclohexane or benzene. Preferably, at least an equimolar amount of base, based on the compound II or III, is employed. The molar ratio of base (calculated as base equivalents) to compounds II or III is in particular in the range from 1:1 to 1:5. Tertiary amines can also be employed in a relatively large excess, for example as solvent or cosolvent.

The reaction is preferably carried out in an organic solvent. Suitable solvents are all solvents which are usually employed for alkylations and which dissolve the reactants in the reaction to a sufficient degree and are for their part inert. Preference is given to aprotic polar solvents, for example ketones such as acetone or methyl ethyl ketone, acetonitrile, dimethyl sulfoxide, amides such as dimethylformamide, dimethylacetamide, N-methylpyrrolidone and cyclic ureas, furthermore aliphatic and alicyclic ethers such as methyl tert-butyl ether, diisopropyl ether, dimethoxyethane, diglycol dimethyl ether, dioxane and tetrahydrofuran, and also aromatic compounds such as toluene, xylene or chlorobenzene, and mixtures of these solvents.

Depending on the reactivity of the substrates and the alkylating agents, the temperature required for the alkylation can be in the range from −80 to +150° C. The alkylation is preferably carried out at temperatures in the range from −20 to +110° C.

Work-up of the reaction product to give the target compound I can be carried out using the methods customary for this purpose. In general, the reaction mixture is initially worked up by extraction, or the solvent used is removed by customary methods, for example by distillation. It is also possible, after dilution of the reaction mixture with water, to extract the target compound I from the reaction mixture using a volatile organic solvent which for its part is removed again by distillation. It is also possible to precipitate the target compound from the reaction mixture by adding water. This gives a crude product which contains the product of value I. For further purification, it is possible to use the customary methods such as crystallization or chromatography, for example on alumina or silica gels. It is also possible to chromatograph the substances obtainable by the process on optically active adsorbates to obtain pure enantiomers.

After the alkylation, the keto group in I can be converted into the thiocarbonyl function using customary sulfurizing agents "S", giving the oxazinethione compounds I where Z=S.

To this end, the compounds I are reacted with a customary sulfurizing agent, for example $P_2S_5$ or Lawesson's reagent [2,4-bis-(4-methoxyphenyl)-1,3-dithia-2,4-diphosphetane2,4-disulfide]. The reaction is preferably carried out in an inert organic solvent, for example one of the ethers or aromatic compounds mentioned above, or mixtures thereof, at temperatures in the range from 0 to 150° C. Corresponding processes are known from U.S. Pat. No. 3,755,582, which is expressly incorporated herein by way of reference.

The starting materials II can be prepared analogously to the literature mentioned above, in the manner shown in scheme 2, starting from α- or ortho-hydroxycarboxylic acid esters of the formula IV. The compound II is in a steady state with its tautomer IV, which is of only minor importance for the subsequent alkylation. In the formulae IV and V, R is, for example, a $C_1$–$C_4$-alkyl group, in particular a methyl group.

Scheme 2:

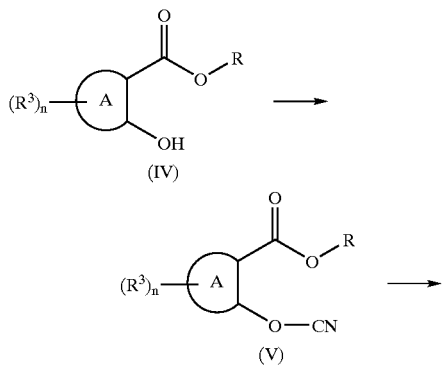

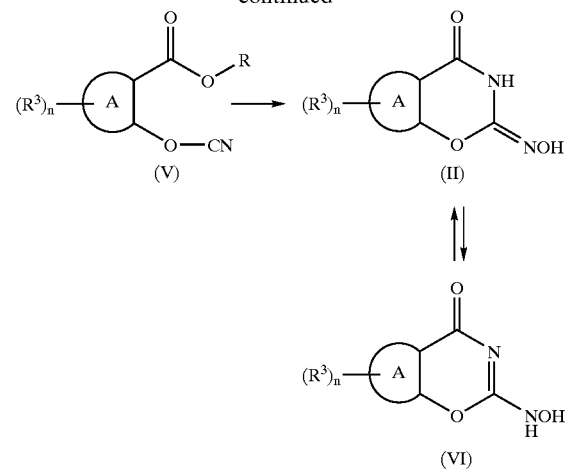

In a first step, an α- or ortho-hydroxycarboxylic acid ester of the formula IV is reacted with a cyanating agent such as cyanogen bromide or cyanogen chloride to give the cyanate V. The cyanating agent is generally employed in stoichiometric amounts, i.e. in equimolar amounts, based on IV, where it is possible to deviate from the exact stoichiometry, but these deviations should preferably be not more than 20 mol %. The cyanation is generally carried out at temperatures in the range from −80 to +100° C., preferably in the range from −40 to +60° C. The reaction is preferably carried out in the presence of an auxiliary base, suitable auxiliary bases being the bases mentioned for the alkylation. Preferred bases are the tertiary amines. The base is preferably employed in equimolar amounts, based on IV, it being possible to deviate from the exact stoichiometry.

The cyanation of IV is generally carried out in an organic solvent. Suitable organic solvents are, in principle, all solvents used in the art in which the reactants are soluble to a sufficient degree during the reaction and which for their part are inert. These include, in particular, aprotic polar solvents, for example ketones, such as acetone or methyl ethyl ketone, nitriles, such as acetonitrile, dimethyl sulfoxide, amides, such as dimethylformamide, dimethylacetamide or N-methylpyrrolidone, cyclic ureas, aliphatic and alicyclic ethers, such as diethyl ether, diisopropyl ether, methyl tert-butyl ether, dimethoxyethane, diglycol dimethyl ether, dioxane or tetrahydrofuran, and also aromatic hydrocarbons, such as toluene, xylenes or chlorobenzene, and mixtures of these solvents.

The cyclization to give the 2-hydroxyiminooxazinone II is carried out by reacting V with hydroxylamine or a customary salt, for example the chloride or sulfate, of hydroxylamine. Here, hydroxylamine is preferably employed in a stoichiometric, i.e. at least equimolar, amount, it also being possible to use an excess of hydroxylamine which, however, should preferably be not more than 50 mol %, based on the stoichiometry of the reaction. The reaction temperatures are generally in the range from −20 to +150° C. and preferably in the range from +20 to 110° C.

The cyclization of V is usually carried out in an organic solvent, for example one of the solvents mentioned above, or a mixture thereof with water. Preferred solvents are alcohols, in particular $C_1$–$C_3$-alkanols, such as methanol, ethanol, n- or isopropanol, and mixtures thereof, and also their mixtures with water. It may be advantageous to change the solvent during the course of the reaction. Thus, it has been found to be expedient to initially start the reaction in an organic solvent, preferably one of the alcohols mentioned above, and then to conclude the reaction in water.

Occasionally, the conversion may be enhanced by adding a base during the course of the reaction. Bases suitable for this purpose are inter alia the carbonates, bicarbonates and hydroxides of alkali metals and alkaline earth metals, for example sodium bicarbonate, sodium carbonate, sodium hydroxide, potassium hydroxide, potassium carbonate, calcium hydroxide and calcium carbonate, and also tertiary amines, such as triethylamine or pyridine.

Instead of hydroxylamine or its salts, it is also possible, as shown in scheme 3, to use O-alkylated hydroxylamines $R^2$—O—$NH_2$ or salts thereof, for example the halides or sulfates, giving the oxazinones I where $R^1$=H. The reaction conditions correspond to the conditions mentioned for the reaction with hydroxylamine.

Scheme 3:

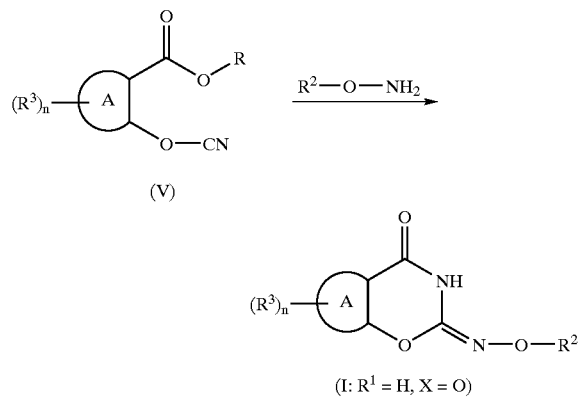

The compounds of the formula I according to the invention can be used as fungicides in their neutral form or in the form of a salt, both acid addition salts and salts of anions of the compounds I with the customary cations being suitable. Suitable agriculturally useful salts are especially the salts of those cations or the acid addition salts of those acids whose cations and anions, respectively, do not adversely affect the fungicidal activity of the compounds I. Thus, suitable cations are in particular the ions of the alkali metals, preferably sodium and potassium, of the alkaline earth metals, preferably calcium, magnesium and barium, and of the transition metals, preferably manganese, copper, zinc and iron, and also the ammonium ion which, if desired, may carry one to four $C_1$–$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and also the anions of $C_1$–$C_4$-alkanoic acids, preferably formate, acetate, propionate and butyrate. They can be formed by reacting I with an acid of the corresponding anion, preferably of hydrochloric acid, hydrobromic acid, sulfuric acid, phosphoric acid or nitric acid.

The novel oxazin(ethi)one compounds of the formula I and their salts are distinguished by an outstanding activity against a broad spectrum of phytopathogenic fungi and can be employed as foliar- and soil-acting fungicides. Some of them are systemically translocated remarkably well and are remarkably active following soil application and in particular following foliar application.

They are of special importance for controlling a large number of fungi on various crop plants such as wheat, rye, barley, oats, rice, maize, grass, bananas, cotton, soybeans, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

*Alternaria* species in vegetables and fruit,

*Botrytis cinerea* (gray mold) in strawberries, vegetables, ornamentals and grapevines,

*Cercospora arachidicola* in peanuts,

*Erysiphe cichoracearum* and *Sphaerotheca fuliginea* in cucurbits,

*Erysiphe graminis* (powdery mildew) in cereals,

*Fusarium* and *Verticillium* species in a variety of plants,

*Helminthosporium* species in cereals,

*Mycosphaerella* species in bananas and peanuts,

*Phytophthora infestans* in potatoes and tomatoes,

*Plasmopara viticola* in grapevines,

*Podosphaera leucotricha* in apples,

*Pseudocercosporella herpotrichoides* in wheat and barley,

*Pseudoperonospora* species in hops and cucumbers,

*Puccinia* species in cereals,

*Pyricularia oryzae* in rice,

*Rhizoctonia* species in cotton, rice and lawns,

*Septoria nodorum* in wheat,

*Sphaerotheca fuliginea* (powdery mildew of cucumber) in cucumbers,

*Uncinula necator* in grapevines,

*Ustilago* species in cereals and sugar cane, and

*Venturia* species (scab) in apples and pears.

The compounds I are also suitable for controlling harmful fungi such as *Paecilomyces variotii* in the protection of materials (for example timber, paper, paint dispersions, fibers or tissue) and in the protection of stored products.

The compounds I are applied by treating the fungi or the plants, seeds or materials to be protected from fungal infection, or the soil, with a fungicidally effective amount of the active ingredients. Application can be effected both before and after infection of the materials, plants or seeds by the fungi.

In general, the fungicidal compositions comprise between 0.1 and 95, preferably between 0.5 and 90, % by weight of active ingredient.

When used in the protection of plants, the application rates are between 0.01 and 2.0 kg of active ingredient per ha, depending on the nature of the desired effect.

In the treatment of seeds, amounts of active ingredient of from 0.001 to 0.1 g, preferably from 0.01 to 0.05 g, are generally required per kilogram of seeds.

When used in the protection of materials or stored products, the application rate of active ingredient depends on the nature of the field of application and the desired effect. Customary application rates in the protection of materials are, for example, from 0.001 g to 2 kg, preferably from 0.005 g to 1 kg, of active ingredient per cubic meter of treated material.

The compounds I can be converted into the customary formulations, for example solutions, emulsions, suspensions, dusts, powders, pastes and granules. The use form depends on the intended purpose in each case; in any case, it should ensure fine and uniform distribution of the compound according to the invention.

The formulations are prepared in a customary fashion, for example by extending the active ingredient with solvents and/or carriers, if appropriate using emulsifiers and dispersants, it also being possible to use other organic solvents as cosolvents if water is used as the diluent. Auxiliaries which can be used for this purpose are essentially: solvents such as aromatics (for example xylene), chlorinated aromatics (for example chlorobenzenes), paraffins (for example mineral oil fractions), alcohols (for example methanol, butanol), ketones (for example cyclohexanone), amines (for example ethanolamine, dimethylformamide) and water; carriers such as natural ground minerals (for example kaolins, clays, talc, chalk) and ground synthetic minerals (for example highly-dispersed silica, silicates); emulsifiers such as nonionic and anionic emulsifiers (for example polyoxyethylene fatty alcohol ether, alkylsulfonates and arylsulfonates) and dispersants such as lignin-sulfite waste liquors and methylcellulose.

Suitable surface-active substances are alkali metal salts, alkaline earth metal salts and ammonium salts of lignosulfonic acid, of naphthalenesulfonic acid, of phenolsulfonic acid, of dibutylnaphthalenesulfonic acid, alkylarylsulfonates, alkyl sulfates, alkylsulfonates, fatty alcohol sulfates and fatty acids, and their alkali metal and alkaline earth metal salts, salts of sulfated fatty alcohol glycol ether, condensates of sulfonated naphthalene and naphthalene derivatives with formaldehyde, condensates of naphthalene or naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Materials which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone or water.

Powders, materials for spreading and dusts can be prepared by mixing or concomitantly grinding the active substances together with a solid carrier.

Granules, for example coated granules, impregnated granules and homogeneous granules, can be prepared by binding the active ingredients to solid carriers. Examples of solid carriers are mineral earths such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers such as, for example, ammonium sulfate, ammonium phosphate, ammonium nitrate, ureas and products of vegetable origin, such as cereal meal, tree bark meal, wood meal and nutshell meal, cellulose powders and other solid carriers.

In general, the formulations comprise between 0.01 and 95% by weight, preferably between 0.1 and 90% by weight, of the active ingredient. The active ingredients are employed in a purity of from 90% to 100%, preferably 95% to 100% (according to NMR spectrum).

Examples of formulations are:

I. 5 parts by weight of a compound according to the invention are mixed intimately with 95 parts by weight of finely divided kaolin. This gives a dust comprising 5% by weight of the active ingredient.

II. 30 parts by weight of a compound according to the invention are mixed intimately with a mixture of 92 parts by weight of pulverulent silica gel and 8 parts by weight of paraffin oil with which the surface of this silica gel has been sprayed. This gives a preparation of the active ingredient with good adhesion (active ingredient content 23% by weight).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (active ingredient content 9% by weight).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (active ingredient content 16% by weight).

V. 80 parts by weight of a compound according to the invention are mixed thoroughly with 3 parts by weight of sodium diisobutylnaphthalene-α-sulfonate, 10 parts by weight of the sodium salt of a lignosulfonic acid from a sulfite waste liquor and 7 parts by weight of pulverulent silica gel, and the mixture is ground in a hammer mill (active ingredient content 80% by weight).

VI. 90 parts by weight of a compound according to the invention are mixed with 10 parts by weight of N-methyl-α-pyrrolidone, which gives a solution which is suitable for use in the form of microdrops (active ingredient content 90% by weight).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100 000 parts by weight of water and finely distributing it therein gives an aqueous dispersion comprising 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20 000 parts by weight of water gives a spray mixture comprising 0.1% by weight of the active ingredient.

IX. 10 parts by weight of the compound according to the invention are dissolved in 63 parts by weight of cyclohexanone, 27 parts by weight of dispersant (for example a mixture of 50 parts by weight of the adduct of 7 mol of ethylene oxide and 1 mol of isooctylphenol and 50 parts by weight of the adduct of 40 mol of ethylene oxide and 1 mol of castor oil). The stock solution is subsequently diluted by distributing in water to the desired concentration, for example to a concentration in the range of from 1 to 100 ppm.

The active compounds can be used as such, in the form of their formulations or the use forms prepared therefrom, for example in the form of directly sprayable solutions, powders, suspensions or dispersions, emulsions, oil dispersions, pastes, dusts, materials for spreading, granules, by means of spraying, atomizing, dusting, spreading or pouring. The use forms depend entirely on the intended uses; in any case, they should ensure the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetters, adhesives, dispersants or emulsifiers. However, it is also possible to prepare concentrates composed of active substance, wetter, adhesive, dispersant or emulsifier and, if appropriate, solvent or oil, and such concentrates are suitable for dilution with water.

The active ingredient concentrations in the ready-to-use preparations can be varied within substantial ranges. In general, they are between 0.0001 and 10%. Frequently, even low application rates of compound I in the ready-to-use preparation suffice, for example from 2 to 200 ppm. Ready-to-use preparations with active ingredient concentrations in the range of from 0.01 to 1% are likewise preferred.

Also, the active ingredients can be used very successfully in the ultra-low-volume method (ULV), it being possible to apply formulations with over 95% by weight of active ingredient, or even the active ingredient without additions.

Various types of oils, or herbicides, fungicides, other pesticides, bactericides, may be added to the active ingredients, if appropriate even only immediately prior to use (tank mix). These agents can be admixed with the agents according to the invention in a weight ratio of 1:10 to 10:1.

In the use form as fungicides, the agents according to the invention may also be present together with other active ingredients, for example with herbicides, insecticides, growth regulators, fungicides, or else with fertilizers. Mixing the compounds I or the compositions comprising them in their use form as fungicides with other fungicides frequently results in a broadened fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropylcarbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis-(dimethylamino)phosphinyl]-3-phenyl-1,2,4-triazole, 2,3-dicyano-1,4-dithioanthraquinone, 2-thio-1,3-dithiolo-[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethylfuran-3-carboxcyclohexylamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene;

strobilurins such as methyl E-methoxyimino-[α-(o-tolyloxy)-o-tolyl]acetate, methyl E-2-{2-[6-(2-cyanophenoxy)pyrimidin-4-yloxy]phenyl}-3-methoxyacrylate, N-methyl-E-methoxyimino-[α-(2-phenoxyphenyl)]acetamide, N-methyl-E-methoxyimino-[α-(2,5-dimethylphenoxy)-o-tolyl]acetamide, methyl E-2-{2-[(2-trifluoromethylpyridyl-6-)oxymethyl]phenyl}-3-methoxyacrylate, methyl (E,E)-methoximino-{2-[1-(3-trifluoromethylphenyl)ethylideneaminooxymethyl]phenyl}acetate, methyl N-(2-{[1-(4-chlorophenyl)-1H-pyrazol-3-yl]oxymethyl}phenyl)-N-methoxycarbamate;

anilinopyrimidines such as N-(4,6-dimethylpyrimidin-2-yl)-aniline, N-[4-methyl-6-(1-propynyl)pyrimidin-2-yl]aniline, N-[4-methyl-6-cyclopropylpyrimidin-2-yl]aniline;

phenylpyrroles such as 4-(2,2-difluoro-1,3-benzodioxol-4-yl)pyrrole-3-carbonitrile;

cinnamamides such as 3-(4-chlorophenyl)-3-(3,4-dimethoxyphenyl)acryloylmorpholine;

and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenylacetyl)-alanine methyl ester, 5-methyl-5-vinyl-3-(3,5-dichlorophenyl)-2,4-dioxo-1,3-oxazolidine, 3-[3,5-dichlorophenyl-(5-methyl-5-methoxymethyl]-1,3-oxazolidine-2,4-dione, 3-(3,5-dichlorophenyl)-1-isopropylcarbamoyl-hydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl) benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl) methyl)-1H-1,2,4-triazole.

The examples below serve to illustrate the invention and are not to be understood as limiting it.

PREPARATION EXAMPLES

Example 1

O-Methyl (6-chloro-3-propyl-4H-1,3-benz[e]oxazin-4(3H)-one)-2-oxime (compound I-A1.2)

1.1 Methyl 2-cyanato-5-chlorobenzoate

At −20° C., 20.0 g (0.198 mol) of triethylamine were added with stirring to 21.0 g (0.198 mol) of cyanogen bromide in 200 ml of acetone. After 5 min, 36.9 g (0.198 mol) of methyl 5-chloro-2-hydroxybenzoate were added, and the mixture was stirred at −20° C. for 30 min. The mixture was filtered, the filter was washed with 200 ml of acetone and the combined organic phases were concentrated under reduced pressure. This gave 34.4 g of the title compound as a yellow solid which was directly reacted further.

1.2 6-Chloro-4H-1,3-benz[e]oxazin-4(3H)-one-2-oxime 34.4 g (0.163 mol) of methyl 2-cyanato-5-chlorobenzoate in 400 ml of methanol and 11.3 g (0.163 mol) of hydroxylamine hydrochloride were stirred at room temperature for 1 h. The solvent was then removed under reduced pressure and the residue was washed with diethyl ether. A solution of 20.5 g of sodium bicarbonate in 400 ml of water was added and the crude product was then stirred for 16 h, filtered off, stirred with 500 ml of water for another 16 h, filtered off and dried. This gave 12.3 g of 6-chloro-4H-1,3-benz[e]oxazin-4(3H)-one-2-oxime.

1.3 6-Chloro-3-propyl-4H-1,3-benz[e]oxazin-4(3H)-one-2-oxime

At room temperature, 0.94 g (23.5 mol) of sodium hydride (60%) was added with stirring to a solution of 5.0 g (23.5 mmol) of 6-chloro-4H-1,3-benz[e]oxazin-4(3H)-one2-oxime in 100 ml of dimethylformamide. 4.3 g (35 mmol) of bromopropane were then added and the mixture was stirred at room temperature for 16 h. The resulting mixture was poured into 100 ml of aqueous sodium dihydrogenphosphate solution (10% strength) and extracted four times with in each case 100 ml of methyl tert-butyl ether. The combined extracts were washed with 100 ml of saturated sodium chloride solution, dried over sodium sulfate and concentrated under reduced pressure. The residue was purified by silica gel chromatography using cyclohexane/ethyl acetate. This gave 1.8 g of the title compound of melting point 144° C.

1.4 O-Methyl (6-chloro-3-propyl-4H-1,3-benz[e]oxazin-4(3H)-one)-2-oxime

At room temperature, a solution of 500 mg (2.0 mmol) of 6-chloro-3-propyl-4H-1,3-benz[e]oxazin-4(3H)-one-2-oxime in 20 ml of dimethylformamide was added immediately, with stirring, to 80 mg (2.1 mmol) of sodium hydride (60%) in 10 ml of dimethylformamide. 430 mg (3.0 mmol) of methyl iodide were then added, and the mixture was stirred at room temperature for 16 h. The resulting mixture was poured into 50 ml of aqueous sodium dihydrogenphosphate solution (10% strength) and extracted four times with in each case 50 ml of methyl tert-butyl ether. The combined extracts were washed with 30 ml of saturated sodium chloride solution, dried over sodium sulfate and concentrated under reduced pressure. This gave the title compound as a crude product which, for purification, was washed successively with diethyl ether and n-hexane. This gave 230 mg of the title compound of melting point 158° C.

Example 2 o-methyl-(6-iodo-3-propyl-4H-1,3-benz[e]oxazin-4(3H)-one)-2-oxime (compound I-A1.4)

2.1 o-methyl-(6-iodo-3-propyl-4H-1,3-benz[e]oxazin-4(3H)-one)-2-oxime 2.0 g (6.6 mmol) of 2-cyanato-5-iodobenzoate, 0.55 g (6.6 mmol) of o-methylhydroxylamine hydrochloride and 0.55 g (6.6 mmol) of sodium bicarbonate were stirred for 1 h in 20 ml of methanol at room temperature. The solvent was then removed under reduced pressure and the residue was added to 10 ml of 10% by weight sodium hydroxide. After 5 min the pH value was adjusted to 6-8 with 10% by weight hydrochloric acid. The precipitate was filtered, washed and dried under reduced pressure. Yield: 2.08 g of a white solid. $^1$H-NMR (d$_6$-DMSO, es sind 2 Isomere zu beobachten) δ=3,70 (s); 7,12 und 7,18 (d); 8,00 (m); 8,05 (s); 11,35 und 11,70 (s).

2.2 o-methyl-(6-iodo-3-propyl-4H-1,3-benz[e]oxazin-4(3H)-one)-2-oxime

While stirring, 2.94 g (9.2 mmol) of o-methyl-(6-iodo-4H-1,3-benz[e]oxazin-4(3H)-one)-2-oxime in 50 ml of dimethylsulfoxide were treated with 1.24 g (1.1 mmol) of potassium tert-butylate at room temperature and afterwards stirred for 5 min, the temperature rising to 30° C. Then, 1.40 g (1.1 mmol) of bromopropane were added and the mixture was stirred for 16 h at room temperature. The mixture was added to 100 ml of an aqueous sodium hydrogenphosphate solution and extracted three times with 100 ml methyl tert-butylether each. The combined extracts were washed once with 30 ml of sodium hydrogenphosphate solution and once with 30 ml of saturated saline solution, dried over sodium sulfate, and concentrated under reduced pressure. Yield: 2.2 g of a white solid. $^1$H-NMR (CDCl$_3$) δ=0,95 (t); 1.75 (m);

3.90 (s); 3.93 (q); 7.00 (d); 7.87 (d); 8.32 (s).

The active compounds of general formula I-A1 in table 4 below were produced analogously.

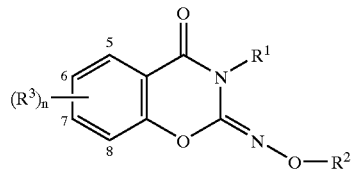

TABLE 4

| No. | R¹ | R² | n | R³ | Physical Data |
|---|---|---|---|---|---|
| I-A1.4 | n-propyl | methyl | 1 | 6-iodo | 126° C. |
| I-A1.8 | n-propyl | ethyl | 1 | 6-iodo | 143° C. |
| I-A1.10 | n-propyl | n-propyl | 1 | 6-chloro | 79° C. |
| I-A1.12 | n-propyl | n-propyl | 1 | 6-iodo | 120° C. |
| I-A1.20 | n-butyl | methyl | 1 | 6-iodo | 113° C. |
| I-A1.24 | n-butyl | ethyl | 1 | 6-iodo | 137° C. |
| I-A1.28 | n-butyl | n-propyl | 1 | 6-iodo | 105° C. |
| I-A1.68 | cyclopropylmethyl | methyl | 1 | 6-iodo | 141° C. |
| I-A1.72 | cyclopropylmethyl | ethyl | 1 | 6-iodo | 119° C. |
| I-A1.76 | cyclopropylmethyl | n-propyl | 1 | 6-iodo | $^1$H-NMR (CDCl$_3$) δ = 0.48 (m); 0.97 (t); 1.36 (m); 1.75 (m); 3.87 (d); 4.00 (t); 7.04 (d); 7.85 (d); 8.32 (s). |
| 1-A1.129 | n-propyl | n-propyl | 0 | — | 52° C. |
| 1-A1.130 | n-propyl | n-propyl | 1 | 6-methyl | $^1$H-NMR (d$_6$-DMSO) d = 0.93 (t); 1.03 (t); 1.68 (m); 2.40 (s); 3.75 (t); 4.02 (t); 7.35 (d); 7.55 (d); 7.70 (s) |
| 1-A1.131 | methyl | n-propyl | 1 | 6-methyl | 50° C. |
| 1-A1.132 | n-propyl | methyl | 1 | 6-methyl | 125° C. |
| 1-A1.133 | n-propyl | methyl | 1 | 6-methoxy | 107° C. |
| 1-A1.134 | cyclopropylmethyl | 2-propyl | 1 | 6-iodo | 88° C. |
| 1-A1.135 | cyclopropylmethyl | cyclopropylmethyl | 1 | 6-iodo | 142° C. |
| 1-A1.136 | n-butyl | cyclopropylmethyl | 1 | 6-iodo | 121° C. |
| 1-A1.137 | n-propyl | cyclopropylmethyl | 1 | 6-iodo | 155° C. |
| 1-A1.138 | n-butyl | 2-propyl | 1 | 6-iodo | 89° C. |
| 1-A1.139 | n-propyl | 2-propyl | 1 | 6-iodo | 90° C. |

USE EXAMPLES

Examples of the Activity Against Harmful Fungi

The fungicidal activity of the compounds of the formula I was demonstrated by the following experiments:

The active compounds were used as aqueous preparations of active compounds which contained the active compound in a concentration of 250 ppm, 63 ppm, 16 ppm and 4 ppm, respectively. The aqueous preparation of active compound was prepared by diluting a stock solution of 10% by weight of active compound, 63% by weight of cyclohexanone and 27% by weight of emulsifier (20 parts by weight of Nekanil® LN (Lutensol® AP6, wetting agent having emulsifying and dispersing action based on ethoxylated alkylphenols) and 10 parts by weight of Wettol® EM (nonionic emulsifier based on ethoxylated castor oil)) with water in the amount required for the desired concentration.

Uses Example 1

Protective Activity Against Mildew of Cucumbers

Leaves of cucumber seedlings of the cultivar "Chinesische Schlange" which had been grown in pots were, at the cotyledon stage, sprayed to runoff point with an aqueous preparation of active compound. 20 hours after the spray coating had dried on, the plants were inoculated with an aqueous spore suspension of mildew of cucumbers (*Sphaerotheca fuliginea*). The plants were then cultivated in a greenhouse at 20–24° C. and 60–80% relative atmospheric humidity for 7 days. The extent of the mildew development was then determined visually in % infection of the cotyledon area.

In this test, even the plants which had been treated with only 4 ppm of the active compound from Example 1 (compound I-A1.2 of Table 1) showed no infection, whereas the untreated plants were 90% infected. Higher application rates gave the same result as 4 ppm. Moreover, the use of the other compounds of table 4 leads to the results as shown in table 5 below.

TABLE 5

| | percentage of infection of leaves at the prescribed concentration of active compound in the aqueous active compound work up | | |
|---|---|---|---|
| Active Compound | 250 ppm | 63 ppm | 16 ppm |
| Compound I - A1.2 | 0 | 0 | 0 |
| Compound I - A1.4 | 0 | 0 | 0 |
| Compound I - A1.8 | 0 | 0 | 0 |
| Compound I - A1.12 | 0 | 0 | 0 |
| Compound I - A1.20 | 0 | 0 | 0 |
| Compound I - A1.24 | 0 | 0 | 0 |
| Compound I - A1.28 | 0 | 0 | 0 |
| Compound I - A1.68 | 0 | 0 | 0 |
| Compound I - A1.72 | 0 | 0 | 0 |
| Compound I - A1.76 | 0 | 0 | 0 |
| Compound I - A1.132 | 0 | 10 | 10 |
| Compound I - A1.133 | 0 | 5 | 10 |
| Compound I - A1.134 | 0 | 0 | 0 |
| Compound I - A1.135 | 0 | 0 | 3 |
| Compound I - A1.136 | 0 | 0 | 0 |
| Compound I - A1.137 | 0 | 0 | 0 |
| Compound I - A1.138 | 0 | 0 | 0 |
| Compound I - A1.139 | 0 | 0 | 0 |
| Untreated | | 90 | |

Use Example 2

Protective Activity Against Mildew of Wheat caused by Erysiphe [syn. Blumeria] graminis forma specialis tritici The first fully developed leaves of the wheat seedlings of the variety "Kanzler" which had been grown in pots were sprayed to runoff point with an aqueous preparation of active compound prepared from a stock solution containing 10% of active compound, 85% of cyclohexanone and 5% of emulsifier. 24 hours after the spray coating had dried on, the plants were inoculated with an aqueous spore suspension of mildew of wheat (Erysiphe [syn. Blumeria] graminis forma specialis. tritici). The plants were then cultivated in a greenhouse at 20–24° C. and 60–90% relative atmospheric humidity. After 7 days the extent of the mildew development was determined visually in % infection of the leaves. The results are shown in table 6

TABLE 6

| Active compound | percentage of infection of leaves at the prescribed concentration of active compound in the aqueous active compound work up | | |
|---|---|---|---|
| | 250 ppm | 63 ppm | 16 ppm |
| Compound I - A1.2 | 0 | 0 | 0 |
| Compound I - A1.4 | 0 | 0 | 0 |
| Compound I - A1.8 | 0 | 0 | 0 |
| Compound I - A1.12 | 0 | 0 | 0 |
| Compound I - A1.20 | 0 | 0 | 0 |
| Compound I - A1.24 | 0 | 0 | 0 |
| Compound I - A1.28 | 0 | 0 | 0 |
| Compound I - A1.68 | 0 | 0 | 0 |
| Compound I - A1.72 | 0 | 0 | 0 |
| Compound I - A1.76 | 0 | 0 | 0 |
| Compound I - A1.133 | 0 | 0 | 20 |
| Compound I - A1.134 | 0 | 0 | 0 |
| Compound I - A1.135 | 0 | 0 | 5 |
| Compound I - A1.136 | 0 | 0 | 0 |
| Compound I - A1.137 | 0 | 0 | 0 |
| Compound I - A1.138 | 0 | 0 | 0 |
| Compound I - A1.139 | 0 | 0 | 0 |
| Untreated | | 85 | |

We claim:

1. An oxazin(ethi)one compound of the formula I

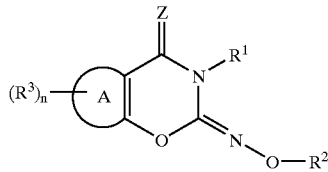

in which the variables Z, A, n, $R^1$, $R^2$ and $R^3$ are as defined below:

Z is oxygen or sulfur,

A is a 5- or 6-membered carbocycle or a 5- or 6-membered heterocycle having 1, 2 or 3 heteroatoms selected from the group consisting of N, O and S, each of which cycles is fused to the oxazin(ethi)one ring via two carbon atoms;

n is a number from 0 to 4;

$R^1$ is hydrogen, is $C_1$–$C_6$-alkyl, $C_2$–$C_6$-alkenyl, $C_2$–$C_6$-alkynyl, which are in each case unsubstituted or substituted by O—$R^4$, C(O)O—$R^5$, $NR^6R^7$, C(O)$NR^6R^7$, S—$R^8$, $C_3$–$C_8$-cycloalkyl, phenyl or by 5- or 6-membered saturated or unsaturated heterocyclyl having 1 to 3 heteroatoms selected from the group consisting of N, O and S, where phenyl and heterocyclyl may be mono-, di- or trisubstituted by $C_1$–$C_6$-haloalkyl, $C_2$–$C_6$-haloalkenyl or $C_2$–$C_6$-haloalkynyl;

$R^2$ is $C_1$–$C_3$-alkyl, $C_1$–$C_3$-haloalkyl or cyclopropylmethyl;

$R^3$ is halogen, cyano, $C_1$–$C_6$-alkyl, $C_1$–$C_6$-haloalkyl, $C_1$–$C_6$alkoxy or $C_1$–$C_6$-haloalkoxy; and in which $R^4$, $R^5$ independently of one another are hydrogen, $C_1$–$C_6$-alkyl, $C_2$–$C_6$-alkenyl, $C_2$–$C_6$-alkynyl, $C_1$–$C_6$-haloalkyl, $C_2$–$C_6$-haloalkenyl, $C_2$–$C_6$-haloalkynyl, hydroxy-$C_1$–$C_4$-alkyl, hydroxycarbonyl-$C_1$–$C_4$-alkyl, $C_1$–$C_4$-alkoxy-$C_1$–$C_4$-alkyl or $C_1$–$C_4$-alkoxycarbonyl-$C_1$–$C_4$-alkyl;

$R^6$, $R^7$ independently of one another are hydrogen, $C_1$–$C_6$-alkyl, $C_1$–$C_6$-alkoxy, $C_2$–$C_6$-alkenyl, $C_2$–$C_6$-alkynyl, $C_1$–$C_6$-haloalkyl, $C_1$–$C_6$-haloalkoxy, $C_2$–$C_6$-haloalkenyl, $C_2$–$C_6$-haloalkynyl, hydroxy-$C_1$–$C_4$-alkyl, hydroxycarbonyl-$C_1$–$C_4$-alkyl, $C_1$–$C_4$-alkoxy-$C_1$–$C_4$-alkyl or $C_1$–$C_4$-alkoxycarbonyl-$C_1$–$C_4$-alkyl;

$R^6$ and $R^7$ together with the nitrogen atom to which they are attached may also form a 5-, 6- or 7-membered saturated N-heterocycle which may contain a further heteroatom selected from the group consisting of O, N and S and/or which may be substituted by 1 to 4 $C_1$–$C_6$-alkyl groups;

$R^8$ represents $C_1$–$C_6$-alkyl, $C_2$–$C_6$-alkenyl, $C_2$–$C_6$-alkynyl, $C_1$–$C_6$-haloalkyl, $C_2$–$C_6$-haloalkenyl, $C_2$–$C_6$-haloalkynyl, hydroxy-$C_1$–$C_4$-alkyl, hydroxycarbonyl-$C_1$–$C_4$-alkyl, $C_1$–$C_4$-alkoxy-$C_1$–$C_4$-alkyl or $C_1$–$C_4$-alkoxycarbonyl-$C_1$–$C_4$alkyl; and the agriculturally useful salts of the oxazin(ethi)one compound I.

2. A compound as claimed in claim 1 where A is a fused benzene, pyridine or thiophene ring.

3. A compound as claimed in claim 1 where $R^1$ is $C_1$–$C_6$-alkyl, $C_2$–$C_6$-alkenyl, $C_1$–$C_6$-haloalkyl, $C_2$–$C_6$-haloalkenyl, $C_1$–$C_4$-alkoxy-$C_1$–$C_4$-alkyl or $C_3$–$C_8$-cycloalkyl-$C_1$–$C_4$-alkyl.

4. A compound as claimed in claim 1 where n is 1, 2, 3 or 4.

5. A compound as claimed in claim 1 where $R^3$ is $C_1$–$C_4$-alkyl, $C_1$–$C_4$-haloalkyl, $C_1$–$C_4$-haloalkoxy or halogen.

6. A compound as claimed in claim 1 where A is a fused benzene ring and the variables Z, $R^1$, $R^2$, $R^3$ and n are as defined below:

Z is oxygen;

$R^1$ is $C_1$–$C_6$-alkyl, $C_2$–$C_6$-alkenyl, $C_1$–$C_6$-haloalkyl, $C_2$–$C_6$-haloalkenyl, $C_1$–$C_4$-alkoxy-$C_1$–$C_4$-alkyl or $C_3$–$C_8$cycloalkyl-$C_1$–$C_4$-alkyl;

$R^2$ is $C_1$–$C_3$-alkyl, $C_1$–$C_3$-haloalkyl or cyclopropylmethyl;

$R^3$ is $C_1$–$C_4$-alkyl, $C_1$–$C_4$-haloalkyl, $C_1$–$C_4$-haloalkoxy or halogen;

n is 1 or 2.

7. A compound as claimed in claim 1, where A is a fused thiophene ring and the variables Z, $R^1$, $R^2$, $R^3$ and n are as defined below:

Z is oxygen;

$R^1$ is $C_1$–$C_6$-alkyl, $C_2$–$C_6$-alkenyl, $C_1$–$C_6$-haloalkyl, $C_2$–$C_6$-haloalkenyl, $C_1$–$C_4$-alkoxy-$C_1$–$C_4$-alkyl or $C_3$–$C_8$cycloalkyl-$C_1$–$C_4$-alkyl;

$R^2$ is $C_1$–$C_3$-alkyl, $C_1$–$C_3$-haloalkyl or cyclopropylmethyl;

$R^3$ is $C_1$–$C_4$-alkyl, $C_1$–$C_4$-haloalkyl, $C_1$–$C_4$-haloalkoxy or halogen;

n is 1 or 2.

8. A composition, which comprises a fungicidally effective amount of at least one compound of the formula I and/or at least one agriculturally useful salt of I as claimed in claim 1 and at least one carrier.

9. A method for controlling phytopathogenic fungi, which comprises treating the fungi or the materials, plants, seeds or the soil threatened by fungal attack with a fungicidally effective amount of at least one compound of the formula I as claimed in claim 1 and/or a salt of I.

* * * * *